(12) United States Patent
Habash

(10) Patent No.: US 10,159,665 B2
(45) Date of Patent: Dec. 25, 2018

(54) PREVENTING AMYLOID PLAQUE FORMATION BY TREATING A HUMAN SUBJECT WITH A NITROXIDE

(71) Applicant: Louis Habash, Irvine, CA (US)

(72) Inventor: Louis Habash, Irvine, CA (US)

( * ) Notice: Subject to any disclaimer, the term of this patent is extended or adjusted under 35 U.S.C. 154(b) by 0 days.

(21) Appl. No.: 15/815,604

(22) Filed: Nov. 16, 2017

(65) Prior Publication Data

US 2018/0092891 A1 Apr. 5, 2018

Related U.S. Application Data

(63) Continuation-in-part of application No. 15/373,239, filed on Dec. 8, 2016, which is a continuation-in-part of application No. 15/078,911, filed on Mar. 23, 2016, now Pat. No. 9,545,398.

(51) Int. Cl.
*A61K 31/445* (2006.01)

(52) U.S. Cl.
CPC ................................. *A61K 31/445* (2013.01)

(58) Field of Classification Search
None
See application file for complete search history.

(56) References Cited

U.S. PATENT DOCUMENTS

| | | |
|---|---|---|
| 8,563,581 B2 | 10/2013 | Habash et al. |
| 8,658,128 B2 | 2/2014 | Altschul et al. |
| 9,101,619 B2 | 8/2015 | Habash et al. |
| 9,545,398 B1 | 1/2017 | Habash |
| 9,579,311 B1 | 2/2017 | Habash |
| 9,700,550 B1 | 7/2017 | Habash |
| 2003/0086916 A1 | 5/2003 | Goligorsky et al. |
| 2005/0175626 A1 | 8/2005 | Delacourte et al. |
| 2006/0159681 A1 | 7/2006 | Lozano et al. |
| 2009/0042937 A1* | 2/2009 | Habash ................ A61K 31/445 514/315 |
| 2009/0131342 A1 | 5/2009 | Ellis |
| 2010/0093828 A1 | 4/2010 | Koya et al. |
| 2010/0179188 A1 | 7/2010 | Rouault et al. |
| 2011/0027351 A1 | 2/2011 | Barenholz et al. |
| 2012/0046314 A1 | 2/2012 | Habash et al. |
| 2012/0059164 A1 | 3/2012 | Perrin-Ninkovic et al. |
| 2012/0165536 A1 | 6/2012 | Ruchelman et al. |

OTHER PUBLICATIONS

Database Caplus Chemical Abstracts Service, Columbus, Ohio, US; Database Accession No. 2016:169540, Abstract of Obulesu et al., Current Drug Metabolism (2016), 17(2), 142-149.*
Shi et al., Neurotherapeutics (2013) 10:340-353.*
Matsuda et al., J Biol Chem. Jun. 5, 2009;284(23):15815-2.*
Antonini et al., An intimate relationship between thyroid hormone and skin: regulation of gene expression, Frontiers in Endocrinology, Aug. 2013, 4(104), doi: 10.3389/fendo.2013.00104.
Askanas et al., Sporadic inclusion-body myositis: A degenerative muscle disease associated with aging, impaired muscle protein homeostasis and abnormal mitophagy, Biochimica et Biophysica Acta (BBA)—Molecular Basis of Disease, Apr. 2015, 1852(4):633-643.
Awad et al., Mechanisms of Disease: molecular genetics of arrhythmogenic right ventricular dysplasia/cardiomyopathy, Nature Clinical Practice Cardiovascular Medicine, May 2008, 5(5):258-267, doi:10.1038/ncpcardio1182.
Bartlett, Dental enamel development: proteinases and their enamel matrix substrates, ISRN Dentistry, Sep. 2013, vol. 2013, Article ID 684607, 24 pages, doi:10.1155/2013/684607.
Beaudry et al., Loss of the desmosomal component perp impairs wound healing in vivo, Dermatology Research and Practice, Jun. 2010, vol. 2010, Article ID 759731, 11 pages, doi:10.1155/2010/759731.
Beaudry et al., Loss of the p53/p63 regulated desmosomal protein perp promotes tumorigenesis, PLoS Genetics, Oct. 2010, 6(10):e1001168.
Bektas et al., Perp and pemphigus: a disease of desmosome destabilization, Journal of Investigative Dermatology, Jul. 2009, 129(7):1606-1608, doi:10.1038/jid.2009.117.
Berkowitz et al., Desmosome signaling—inhibition of p38mapk prevents pemphigus vulgaris IgG-induced cytoskeleton reorganization, The Journal of Biological Chemistry, Jun. 2005, 280(25):23778-23784.
De Jong et al., Fatty acids, lipid mediators, and T-cell function, Frontiers in Immunology, Oct. 2014, 13(5):483, 7 pages.
Dusek et al., Desmosomes: new perpetrators in tumour suppression, Nature Reviews Cancer, May 2011, 11(5): 317-323, doi:10.1038/nrc3051.
Fenutría et al., Role of CD5/CD5L interactions in the homeostasis of regulatory lymphocyte subpopulations and the control of autoimmune disorders, Journal of Translational Medicine, Nov. 2011, 9(Suppl 2):O6.
Fierabracci et al., The double role of p53 in cancer and autoimmunity and its potential as therapeutic target, International Journal of Molecular Sciences, Nov. 2016, International Journal of Molecular Sciences, 17(12):1975.
Gantt et al., Oxidative responses of human and murine macrophages during phagocytosis of leishmania chagasi, The Journal of Immunology, Jul. 2001, 167:893-901.
Garrod et al., Desmosome structure, composition and function, Biochimica et Biophysica Acta, Mar. 2008, 1778(3):572-587.
Gaublomme et al., Single-cell genomics unveils critical regulators of th17 cell pathogenicity, Cell, Dec. 2015, 163(6):1400-1412, doi:10.1016/j.cell.2015.11.009.
Gegg et al., Silencing of pink1 expression affects mitochondrial dna and oxidative phosphorylation in dopaminergic cells, PLoS One, Mar. 2009, 4(3):e4756.

(Continued)

*Primary Examiner* — Karl J Puttlitz

(74) *Attorney, Agent, or Firm* — Knobbe, Martens, Olson & Bear, LLP

(57) ABSTRACT

Disclosed herein are embodiments of a method of inhibiting amyloid plaque deposition. In some embodiments, the method comprises: administering to an individual known to have a decreased expression level of Bri3 an amount of a nitroxide antioxidant effective to increase the BRI3 expression level relative to the decreased expression level, whereby the increased expression level of Bri3 inhibits amyloid plaque deposition via inhibition of amyloid precursor protein processing.

4 Claims, No Drawings

(56) References Cited

OTHER PUBLICATIONS

Guo et al., Bag5 protects neuronal cells from amyloid [beta]-induced cell death, Journal of Molecular Neuroscience, Apr. 2015, 55(4):815-820.
Halaby, Apoptosis and autoimmune disorders, Autoimmune Diseases—Contributing Factors, Specific Cases of Autoimmune Diseases, and Stem Cell and Other Therapies, Dr. James Chan (Ed.), Jul. 2012, InTech, DOI: 10.5772/48164, 18 pages.
Hildeman et al., T cell apoptosis and reactive oxygen species, The Journal of Clinical Investigation, Mar. 2003, 111(5):575-581, doi:10.1172/JCI200318007.
Hsu et al., Inhibition of macrophage scavenger receptor activity by tumor necrosis factor-a is transcriptionally and post-transcriptionally regulated, The Journal of Biological Chemistry, Mar. 1996, 271(13):7767-7773.
Iwakura et al., The IL-23/IL-17 axis in inflammation, The Journal of Clinical Investigation, May 2006, 116(5): 1218-1222.
Jheon et al., PERP regulates enamel formation via effects on cell-cell adhesion and gene expression, Journal of Cell Science, Mar. 2011, 124(5):745-754.
Ji et al., Arthritis critically dependent on innate immune system players, Immunity, Feb. 2002, 16(2):157-168.
Johnson et al., Desmosomes: regulators of cellular signaling and adhesion in epidermal health and disease, Cold Spring Harbor Perspectives in Medicine, Nov. 2014, 4(11):a015297.
Jung et al., Stability of water-soluble and lipid-soluble paramagnetic probes in Bacillus subtilis, Biochimica et Biophysica Acta (BBA)—General Subjects, Oct. 1998, 1425(2):387-397.
Kowalczyk et al., Structure, function and regulation of desmosomes, Progress in Molecular Biology and Translational Science, 2013, 116: 95-118, doi:10.1016/B978-0-12-394311-8.00005-4.
Lee et al., Mutant p53 promotes ovarian cancer cell adhesion to mesothelial cells via integrin [beta]4 and Akt signals, Scientific Reports (Nature Publisher Group), Jul. 2015, 5:12642, DOI: 10.1038/srep12642.
Linares et al., Inhibition of in vivo leishmanicidal mechanisms by tempol: Nitric oxide down-regulation and oxidant scavenging, Free Radical Biology and Medicine, Apr. 2008, 44(8):1668-1676.
Luckheeram et al., CD4+T cells: differentiation and functions, Clinical and Developmental Immunology, Mar. 2012, vol. 2012, Article ID 925135, 12 pages, doi: 10.1155/2012/925135.
Mahoney et al., Desmosomes and desmosomal cadherin function in skin and heart diseases—advancements in basic and clinical research, Dermatology Research and Practice, Sep. 2010, vol. 2010, Article ID 725647, 3 pages, doi:10.1155/2010/725647.
Marques et al., The requirement for perp in postnatal viability and epithelial integrity reflects an intrinsic role in stratified epithelia, Journal of Investigative Dermatology, Jan. 2006, 126(1):69-73, doi:10.1038/sj.jid.5700032.
Matsuda et al., CD74 interacts with APP and suppresses the production of A [beta], Molecular Neurodegeneration, Oct. 2009, 4(1):41, doi:10.1186/1750-1326-4-41.
Morais et al., Parkinson's disease mutations in PINK1 result in decreased Complex I activity and deficient synaptic function, EMO Molecular Medicine, May 2009, 1(2):99-111.
Numata et al., Mechanisms of enzymatic degradation of amyloid beta microfibrils generating nanofilaments and nanospheres related to cytotoxicity, Biochemistry, Apr. 2010, 49(15): 3254-3260, doi:10.1021/bi902134p.
Ouyang, The biological functions oft helper 17 cell effector cytokines in inflammation, Immunity, Apr. 2008, 28(4):454-467, doi:10.1016/j.immuni.2008.03.004.
Petit et al., Wild-type pink1 prevents basal and induced neuronal apoptosis, a protective effect abrogated by parkinson disease-related mutations, The Journal of Biological Chemistry, Oct. 2005, 280(40):34025-34032.
Rosenblum et al., Treating Human Autoimmunity: Current Practice and Future Prospects, Science Translational Medicine, Mar. 2012, 4(125):1255r1, doi:10.1126/scitranslmed.3003504.
Saido et al., Proteolytic degradation of amyloid [beta]-protein, Cold Spring Harbor Perspectives in Medicine, Jun. 2012, 2(6):a006379.
Sanjurjo et al., The human CD5L/AIM-CD36 axis: A novel autophagy inducer in macrophages that modulates inflammatory responses, Autophagy, Mar. 2015, 11(3)487-502.
Sanjurjo et al., AIM/CD5L: a key protein in the control of immune homeostasis and inflammatory disease, Journal of Leukocyte Biology, Aug. 2015, 98(2):173-184.
T cell mediated autoimmune diseases, Immunopaedia.org, https://www.immunopaedia.org.za/immunology/advanced/9-t-cell-mediated-autoimmune-diseases/, accessed Dec. 14, 2017, 9 pages.
Uittenbogaard et al., Transcriptional repression of p53 by human t-cell leukemia virus type I tax protein, The Journal of Biological Chemistry, Dec. 1995, 270(48): 28503-28506.
Vergoni et al., DNA damage and the activation of the p53 pathway mediate alterations in metabolic and secretory functions of adipocytes, Diabetes, Oct. 2016, 65(10):3062-3074.
Voudouri et al., Data on the putative role of p53 in breast cancer cell adhesion: Technical information for adhesion assay, Data in Brief, Dec. 2016, 9:568-572.
Wang et al., CD5L/AIM regulates lipid biosynthesis and restrains Th17 cell pathogenicity, Cell, Dec. 2015, 163(6):1413-1427.
Wickham et al., [Beta]-Amyloid protein converting enzyme 1 and brain-specific type II membrane protein BRI3: binding partners processed by furin, Journal of Neurochemistry, Jan. 2005, 92(1):92-102.
Williams, Amyloid beta and cardiovascular disease, Journal of the American College of Cardiology, Mar. 2015, 65(9):917-919.
Wood-Kaczmar et al., PINK1 is necessary for long term survival and mitochondrial function in human dopaminergic neurons, PLoS One, Jun. 2008, 3(6):e2455.
Zhang et al., Th17 cell frequency and IL-17 concentration correlate with pre- and postoperative pain sensation in patients with intervertebral disk degeneration, Orthopedics, Jul. 2014, 37(7):e685-e691.
Durcan et al., The three "P"s of mitophagy: PARKIN, PINK1, and post-translational modifications, Genes & Development, May 2015, 29(10):989-999, http://doi.org/10.1101/gad.262758.115.
Gispert et al., Parkinson phenotype in aged PINK1-deficient mice is accompanied by progressive mitochondrial dysfunction in absence of neurodegeneration, PLoS one, Jun. 2009, 4(6):e5777, https://doi.org/10.1371/journal.pone.0005777.
Kaden et al., Autophagy, mitochondrial dynamics and retinal diseases, Asia-Pacific Journal of Ophthalmology (Philadelphia, Pa.), Sep. 2013, 2(5), http://doi.org/10.1097/APO.0b013e31829d3e33.
Khalil et al., PINK1-induced mitophagy promotes neuroprotection in Huntington's disease. Cell Death & Disease, Jan. 2015, 6(1):e1617, http://doi.org/10.1038/cddis.2014.581.
Lazarou et al., The ubiquitin kinase PINK1 recruits autophagy receptors to induce mitophagy, Nature, Aug. 2015, 524(7565):309-314, http://doi.org/10.1038/nature14893.
Matsuda et al., Function and characteristics of PINK1 in mitochondria, Oxidative Medicine and Cellular Longevity, Feb. 2013, 2013, Article ID 601587, 6 pages, doi:10.1155/2013/601587.
Mattson et al., Mitochondria in neuroplasticity and neurological disorders, Neuron, Dec. 2008, 60(5):748-766, https://doi.org/10.1016/j.neuron.2008.10.010.
Narendra et al., PINK1 is selectively stabilized on impaired mitochondria to activate Parkin, Jan. 2010, 8(1):e1000298.
Narendra et al., Targeting mitochondrial dysfunction: role for PINK1 and parkin in mitochondrial quality control, Antioxidants & Redox Signaling, May 2011, 14(10):1929-1938, http://doi.org/10.1089/ars.2010.3799.
Oliveira, Nature and cause of mitochondrial dysfunction in Huntington's disease: focusing on huntingtin and the striatum, Journal of Neurochemistry, Apr. 2010, 114(1):1-12, doi:10.1111/j.1471-4159.2010.06741.x.
Redmann et al., Mitophagy mechanisms and role in human diseases, The International Journal of Biochemistry & Cell Biology, Aug. 2014, 53:127-133, http://doi.org/10.1016/j.biocel.2014.05.010.
Spano et al., The possible involvement of mitochondrial dysfunctions in Lewy body dementia: a systematic review, Functional Neurology, Jul. 2015, 30(3):151-158, http://doi.org/10.11138/FNeur/2015.30.3.151.

(56) References Cited

OTHER PUBLICATIONS

Steer et al., Beyond mitophagy: cytosolic PINK1 as a messenger of mitochondrial health, Antioxidants & Redox Signaling, Apr. 2015, 22(12)1047-1059, http://doi.org/10.1089/ars.2014.6206.
Tang et al., The critical roles of mitophagy in cerebral ischemia, Protein & Cell, Oct. 2016, 7(10):699-713, https://doi.org/10.1007/513238-016-0307-0.
Vives-Bauza et al., PINK1-dependent recruitment of Parkin to mitochondria in mitophagy, Proceedings of the National Academy of Sciences of the United States of America, Jan. 2010, 107(1):378-383.
Williams et al., Targeting pink/-parkin-mediated mitophagy for treating liver injury, Pharmacological Research, Dec. 2015, 102:264-269, http://doi.org/10.1016/j.phrs.2015.09.020.
Wong et al., Temporal dynamics of PARK2/parkin and OPTN/optineurin recruitment during the mitophagy of damaged mitochondria, Autophagy, Feb. 2015, 11(2):422-424, http://doi.org/10.1080/15548627.2015.1009792.
Zhang et al., Parkin regulation and neurodegenerative disorders, Frontiers in Aging Neuroscience, Jan. 2016, 7:248, doi: 10.3389/fnagi.2015.00248.
Amézaga et al., J. Leukoc. Human scavenger protein AIM increases foam cell formation and CD36-mediated oxLDL uptake, Biol. (2014) 95(3):509-20.
Arai et al., A role for the apoptosis inhibitory factor AIM/Spα/Api6 in atherosclerosis development, Cell Metab. (2005) 1:201-213.
Arakawa et al. The C-Terminal BAG Domain of BAG5 Induces Conformational Changes of the Hsp70 Nucleotide-Binding Domain for ADP-ATP Exchange, Structure (2010) 18(3):309-19.
Arakawa, p53, apoptosis and axon-guidance molecules, Cell Death Differ. (2005) 12(8):1057-65.
Attardi et al., PERP, an apoptosis-associated target of p53, is a novel member of the PMP-22/gas3 family, Genes Dev. (2000) 14(6):704-18.
Bandrés et al., A gene signature of 8 genes could identify the risk of recurrence and progression in Dukes' B colon cancer patients, Oncology Reports (2007) 17(5):1089-1094.
Beaudry et al., Loss of the p53/p63 Regulated Desmosomal Protein Perp Promotes Tumorigenesis, PLoS Genet. (2010) 6(10): e1001168.
Chen et al., PERP gene therapy attenuates lung cancer xenograft via inducing apoptosis and suppressing VEGF, Cancer Biol. Ther. (2011) 12(12):1114-19.
Davies et al., PERP expression stabilizes active p53 via modulation of p53-MDM2 interaction in uveal melanoma cells, Cell Death and Disease (2011) 2:e136.
Davies et al., P53 apoptosis mediator PERP: localization, function and caspase activation in uveal melanoma, J. Cell .Mol. Med. (2009) 13:1995-2007.
Du et al., Decreased PERP Expression on Peripheral Blood Mononuclear Cells from Patient with Rheumatoid Arthritis Negatively Correlates with Disease Activity, Clinical and Developmental Immunology (2013) 2013:256462.
Dusek et al., Deficiency of the p53/p63 target Perp alters mammary gland homeostasis and promotes cancer, Breast Cancer Res. (2012) 14(2):R65.
Flachsbart et al., Investigation of genetic susceptibility factors for human longevity—A targeted nonsynonymous SNP study, Mutat. Res. (2010) 694(1-2):13-19.
Fotinopoulou et al., BR12 Interacts with Amyloid Precursor Protein (APP) and Regulates Amyloid β (Aβ) Production, J. Biol. Chem. (2005) 280(35):30469-72.
Glass et al. Gene expression changes with age in skin, adipose tissue, blood and brain, Genome Biology 2013, 14:R75.
Gollob et al., Gene Expression Chnages and Signaling Events Associated with the Direct Antimelanoma Effect of IFN-γ, Cancer Res. (2005) 65(19):8869-77.
Gong et al., BRI3 associates with SCG10 and attenuates NGF-induced neurite outgrowth in PC12 cells, BMB Rep. (2008) 41(4):287-93.
Hallstrom et al., PERP, a Host Tetraspanning Membrane Protein, is Required for *Salmonella*-Induced Inflammation, Cell Microbiol. (2015) 17(6):843-59.
Haruta et al., Association of AIM, a Novel Apoptosis Inhibitory Factor, with Hepatitis via Supporting Macrophage Survival and Enhancing Phagocytotic Function of Macrophages, J. Biol. Chem. (2001) 276:22910-22914.
He et al., Akt-phosphorylated PIKE-A inhibits UNC5B-induced apoptosis in cancer cell lines in a p53-dependent manner, Mol. Biol. Cell. (2011) 22(11):1943-54.
Hildebrandt et al., Identification of THW, a putative new tumor suppressor gene, Anticancer Res. (2000) 20(5A):2801-9.
Ihrie et al., Perp Is a p63-Regulated Gene Essential for Epithelial Integrity, Cell (2005) 120(6):843-56.
Ihrie et al., Perp Is a Mediator of p53-Dependent Apoptosis in Diverse Cell Types, Current Biology (2003) 13(22):1985-1990.
Joseph et al. LXR-Dependent Gene Expression Is Important for Macrophage Survival and the Innate Immune Response, Cell (2004) 119:299-309.
Kalia et al., BAG5 Inhibits Parkin and Enhances Dopaminergic Neuron Degeneration, Neuron (2004) 44(6):931-945.
Kelly et al., Germline Variation in Apoptosis Pathway Genes and Risk of Non-Hodgkin's Lymphoma, Cancer Epidemiol. Biomarkers. Prev. (2010) 19(11):2847-2858.
Kohno et al., Interleukin-17 gene expression in patients with rheumatoid arthritis, Modern Rheumatology (2008) 18(1):15-22.
Kong et al., Loss of the p53/p63 Target PERP is an Early Event in Oral Carcinogenesis and Correlates with Higher Rate of Local Relapse, Oral Surg. Oral Med. Oral Pathol. Oral Radiol. (2013) 115(1):95-103.
Kong et al., Interactional expression of netrin-1 and its dependence receptor UNC5B in prostate carcinoma, Tumor Biol. (2013) 34(5):2765-72.
Kuwata et al., Role of AIM in *Corynebacterium*-induced granuloma formation in mice, Comp. Hepatol. (2004) 3, Suppl. 1:S44.
Liu et al., PKC α regulates netrin-1/UNC5B-mediated survival pathway in bladder cancer, BMC Cancer. (2014) 14: 93.
Liu et al., Clinical significance of UNC5B expression in bladder cancer, Tumor Biol. (2013) 34(4):2099-108.
Llambi et al., The dependence receptor UNC5H2 mediates apoptosis through DAP-kinase, EMBO J. (2005) 24(6):1192-201.
Lowe et al., p53 is required for radiation-induced apoptosis in mouse thymocytes, Nature (1993) 362(6423):847-849.
Lu et al. Gene regulation and DNA damage in the ageing human brain, Nature (2004) 429:883-891.
Marques et al., Mice Lacking the p53/p63 Target Gene Perp Are Resistant to Papilloma Development, Cancer Res. (2005) 65:6551-6.
Matsuda et al, BR13 Inhibits Amyloid Precursor Protein Processing in a Mechanistically Distinct Manner from Its Homologue Dementia Gene BR12-, J. Biol. Chem. (2009) 284(23):15815-25.
Matsuda et al., The Familial Dementia BR12 Gene Binds the Alzheimer Gene Amyloid-β Precursor Protein and Inhibits Amyloid-β Production, J. Biol. Chem. (2005) 280(32):28912-16.
Matsuda et al., BR12 Inhibits Amyloid β-Peptide Precursor Protein Processing by Interfering with the Docking of Secretases to the Substrate, J. Neurosci. (2008) 28(35):8668-76.
Miyazaki et al., Increased Susceptibility of Thymocytes to Apoptosis in Mice Lacking AIM, a Novel Murine Macrophage-derived Soluble Factor Belonging to the Scavenger Receptor Cysteine-rich Domain Superfamily, J. Exp. Med. (1999) 189:413-422.
Nguyen et al., Loss of the Desmosomal Protein Perp Enhances the Phenotypic Effects of Pemphigus Vulgaris Autoantibodies, J. Invest. Dermatol. (2009) 129(7):1710-8.
Nowak et al., Perp is required for tissue-specific cell survival during zebrafish development, Cell Death and Differentiation (2005) 12(1):52-64.
Okazaki et al., Clinical significance of UNC5B expression in colorectal cancer, Int. J. Oncol. (2012) 40(1):209-16.
Paraoan et al, Expression of p53-induced apoptosis effector PERP in primary uveal melanomas: Downregulation is associated with aggressive type, Exp. Eye. Res. (2006) 83(4):911-19.

(56) References Cited

OTHER PUBLICATIONS

Sanjurjo et al., The Scavenger Protein Apoptosis Inhibitor of Macrophages (AIM) Potentiates the Antimicrobial Response against *Mycobacterium tuberculosis* by Enhancing Autophagy, LoS One. (2013) 8(11):e79670.
Sarrias et al., A Role for Human SPα as a Pattern Recognition Receptor, J. Biol. Chem. (2005) 280:35391-35398.
Thiebault et al., The netrin-1 receptors UNC5H are putative tumor suppressors controlling cell death commitment, Proc. Natl. Acad. Sci. U.S.A. (2003) 100(7):4173-78.
Wang et al., Bags Protects against Mitochondrial Oxidative Damage through Regulating PINK1 Degradation, PLoS One. (2014) 9(1):e86276.
Wu et al., bri3, a novel gene, participates in tumor necrosis factor-α-induced cell death, Biochem. Biophys. Res. Commun. (2003) 311(2):518-24.
Yamazaki et al., Circulating AIM as an Indicator of Liver Damage and Hepatocellular Carcinoma in Humans, PLoS One. (2014) 9(10):e109123.
Zhan et al., PKCα is involved in the progression of kidney carcinoma through regulating netrin-1/UNC5B signaling pathway, Tumor Biol. (2013) 34(3):1759-66.
Zhang et al., [Down-regulated expression of UNC5b related to hepatocellular carcinoma angiogenesis]. Zhonghua Wai Ke Za Zhi (2009) 47(20):1569-73.
Zou, et al., "Liseria monocytogenes Infection Induces Prosurvival Metabolic Signaling in Macrphages", Infection and Immunity, Apr. 2011, vol. 79, No. 4, pp. 1526-1535.
International Search Report and Written Opinion for PCT Application No. PCT/US2017/023681, dated Jun. 16, 2017.
FDA-approved treatments for Alzheimer's, alz.org®, TS-0087, 1-5.
Connor, et al., "Brain-derived neurotrophic factor is reduced in Alzheimer's disease." Brain Res Mol Brain Res. Oct. 3, 1997;49(1-2):71-81, Abstract.
Erickson, et al., : Brain-Derived Neurotrophic Factor Is Associated with Age-Related Decline in Hippocampal Volume Journal of Neuroscience Apr. 14, 2010, 30 (15) 5368-5375.
Montagne, et al., "Alzheimer's disease: A matter of blood—brain barrier dysfunction?" Journal of Experimental Medicine, 2017 Archive, 23, Oct. 2017, 217(11):3151.
Narisawa-Saito, et al., "Regional specificity of alterations in NGF, BDNF and NT-3 levels in Alzheimer's disease." Neuroreport. Nov. 25, 1996;7(18):2925-8, Abstract.
Berislav V. Zlokovic, "Neurovascular pathways to neurodegeneration in Alzheimer's disease and other disorders" *Nat Rev Neurosci.*; May 28, 2014, 12(12): 723-738.
Liang, et al., "Neuroprotective effects of TEMPOL in central and peripheral nervous system models of Parkinson's disease", Biochemical Pharmacology, vol. 70 (2005), pp. 1371-1381.
Linares, et al., "Tempol Moderately Extends Survival in a Hsod1$^{G93A}$ ALS Rat Model by Inhibiting Neuronal Cell Loss, Oxidative Damage and Levels of Non-Native Hsod1$^{G93A}$ Form" PLOS One, Feb. 2013, Vo.I 8, Issue 2, e55868, pp. 1-12.
Sandhir, et al., "4-hydroxy tempo improves mitochondrial and neurobehavioral deficits in experimental model of Huntington's disease" Synapse, vol. 69, Issue 3, Mar. 2015, pp. 128-138, Abstract.

* cited by examiner

PREVENTING AMYLOID PLAQUE FORMATION BY TREATING A HUMAN SUBJECT WITH A NITROXIDE

RELATED APPLICATIONS

The present application is a Continuation-in-Part of U.S. application Ser. No. 15/373239, filed on Dec. 8, 2016, which is a Continuation of U.S. application Ser. No. 15/078911, filed on Mar. 23, 2016. The content of each of these related applications is hereby incorporated by reference in its entirety.

BACKGROUND

Field

The present disclosure relates generally to the field of treating diseases and more particularly to treating human subjects with decrease in gene expression (such as age-related decrease in gene expression) and diseases associated with decrease in gene expression with a nitroxide.

Description of the Related Art

Apoptosis is a process of programmed cell death that occurs in multicellular organisms. Through apoptosis, cells commit suicide as a way to clear unwanted or damaged cells or to prevent uncontrolled growth. Thus, apoptosis plays an essential role in tissue development and function. Dysregulation in the apoptotic pathway, for example decrease or increase in apoptosis, can lead to a number of diseases and conditions, for example, cancers, autoimmune diseases, inflammatory diseases, and infections.

SUMMARY

Some embodiments disclosed herein provide methods for increasing gene expression. The methods, in some embodiments, include administering to a human subject an effective amount of a nitroxide antioxidant resulting in an increased expression level of a gene (e.g., a gene associated with the apoptosis pathway). In some embodiments, the methods further comprise: identifying the human subject. In some embodiments, the human subject is over the age of 35 and has a decrease expression level of a gene (e.g., a gene associated with the apoptosis pathway). In some embodiments, the gene is selected from the group consisting of: Cd51, Perp, Unc5b, Bag5 and Bri3. In some embodiments, the human subject is over the age of 45. In some embodiments, the human subject is over the age of 55. In some embodiments, the human subject is over the age of 65. In some embodiments, the expression level of the gene in a skin tissue is increased. In some embodiments, the expression level of the gene in an adipose tissue is increased. In some embodiments, the expression level of the gene in blood is increased. In some embodiments, the expression level of the gene in a neuronal tissue is increased. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for increasing the expression level of a gene in a human subject in need thereof, comprising: administering to a human subject an effective amount of a nitroxide antioxidant, whereby the expression level of a gene (e.g., a gene associated with the apoptosis pathway) is increased. In some embodiments, the methods further comprise: identifying the human subject. In some embodiments, the human subject has a decreased expression level of the gene (e.g., a gene associated with the apoptosis pathway). In some embodiments, the gene is selected from the group consisting of: Cd51, Perp, Unc5b, Bag5 and Bri3. In some embodiments, the decreased expression level of the gene is age-related. In some embodiments, the human subject is over the age of 35. In some embodiments, the human subject is over the age of 45. In some embodiments, the human subject is over the age of 55. In some embodiments, the human subject is over the age of 65. In some embodiments, the decreased expression level of the gene is disease-related. In some embodiments, the disease is selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the disease is age-related. In some embodiments, the expression level of the gene in a skin tissue is increased. In some embodiments, the expression level of the gene in an adipose tissue is increased. In some embodiments, the expression level of the gene in blood is increased. In some embodiments, the expression level of the gene in a neuronal tissue is increased. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for reducing risk of a disease in a human subject in need thereof, comprising: administering to a human subject an effective amount of a nitroxide antioxidant, whereby the expression level of a gene (e.g., a gene associated with the apoptosis pathway) is increased. In some embodiments, the methods further comprise: identifying the human subject. In some embodiments, the human subject is over the age of 35 having an increased risk of a disease due to a decreased expression level of the gene (e.g., a gene associated with the apoptosis pathway). In some embodiments, the disease is selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the gene is selected from the group consisting of: Cd51, Perp, Unc5b, Bag5 and Bri3. In some embodiments, the human subject is over the age of 45. In some embodiments, the human subject is over the age of 55. In some embodiments, the human subject is over the age of 65. In some embodiments, the expression level of the gene in a skin tissue is increased. In some embodiments, the expression level of the gene in an adipose tissue is increased. In some embodiments, the expression level of the gene in blood is increased. In some embodiments, the expression level of the gene in a neuronal tissue is increased. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods comprising: administering to a human subject an effective amount of a nitroxide antioxidant, whereby the expression level of a gene (e.g., a gene associated with the apoptosis pathway) is increased. In some embodiments, the methods further comprise: identifying the human subject. In some embodiments, the human subject has or is at risk of developing a cancer and is in need of an increased expression level of a gene (e.g., a gene associated with the apoptosis pathway). In some embodiments, the cancer can be selected from the group consisting of bladder cancer, colorectal cancer, hepatocellular carcinoma, prostate carcinoma, and kidney carcinoma. In some embodiments, the gene is selected from the group consisting of: Cd51, Perp, Unc5b, Bag5 and Bri3. In some embodiments, the cancer is age-related. In some embodiments, the human subject is over the age of 35. In some embodiments, the human subject is over the age of 45. In some embodiments, the human subject is over the age of 55. In some embodiments, the human subject is over the age of 65. In some embodiments, the expression level of the gene in a skin tissue is increased. In some embodiments, the expression level of the gene in an adipose tissue is increased. In some embodiments, the expression level of the gene in blood is increased. In some embodiments, the expression level of the gene in a neuronal tissue is increased. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods comprising: administering to a human subject an effective amount of a nitroxide antioxidant, wherein the expression level of a gene associated (e.g., a gene associated with the apoptosis pathway) is increased. In some embodiments, the methods further comprise: identifying the human subject. In some embodiments, the human subject has or is at risk of developing an autoimmune disease and is in need of an increased expression level of the gene (e.g., a gene associated with the apoptosis pathway). In some embodiments, the autoimmune disease can be selected from the group consisting of rheumatoid/osteoid arthritis, systemic lupus erythematosus (SLE), inflammatory bowel disease, multiple sclerosis, atherosclerosis, and osteoporosis. In some embodiments, the gene is selected from the group consisting of: Cd51, Perp, Unc5b, Bag5 and Bri3. In some embodiments, the gene is Cd51. In some embodiments, the autoimmune disease is age-related. In some embodiments, the human subject is over the age of 35. In some embodiments, the human subject is over the age of 45. In some embodiments, the human subject is over the age of 55. In some embodiments, the human subject is over the age of 65. In some embodiments, the expression level of the gene in a skin tissue is increased. In some embodiments, the expression level of the gene in an adipose tissue is increased. In some embodiments, the expression level of the gene in blood is increased. In some embodiments, the expression level of the gene in a neuronal tissue is increased. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for a disease associated with a decreased apoptosis in a patient in need thereof, comprising: administering to a human subject an effective amount of a nitroxide antioxidant, whereby the expression level of a gene (e.g., a gene associated with the apoptosis pathway) is increased. In some embodiments, the methods further comprise: identifying the human subject. In some embodiments, the human subject has or is at risk of developing the disease associated with a decreased expression of the gene (e.g., a gene associated with the apoptosis pathway). In some embodiments, the disease can be selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the gene is selected from the group consisting of: Cd51, Perp, Unc5b, Bag5 and Bri3. In some embodiments, the human subject is over the age of 35. In some embodiments, the human subject is over the age of 45. In some embodiments, the human subject is over the age of 55. In some embodiments, the human subject is over the age of 65. In some embodiments, the expression level of the gene in a skin tissue is increased. In some embodiments, the expression level of the gene in an adipose tissue is increased. In some embodiments, the expression level of the gene in blood is increased. In some embodiments, the expression level of the gene in a neuronal tissue is increased. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for treating an individual in need thereof, comprising: administering to an individual an effective amount of a nitroxide antioxidant to increase the level of expression of a gene (e.g., a gene associated with the apoptosis pathway). In some embodiments, the methods further comprise: identifying the individual. In some embodiments, the individual is over the age of 35 and is in need of an increased expression level of the gene (e.g., a gene associated with the apoptosis pathway). In some embodiments, the gene is selected from the group consisting of: Cd51, Perp, Unc5b, Bag5 and Bri3. In some embodiments, the human subject is over the age of 45. In some embodiments, the human subject is over the age of 55. In some embodiments, the human subject is over the age of 65. In some embodiments, the human subject has a decrease expression level of the gene. In some embodiments, the individual has or is at risk of developing an age-related condition. In some embodiments, the age-related condition comprises increased senescence in a tissue. In some embodiments, the age-related condition comprises inactivation of the apoptosis pathway in a tissue. In some embodiments, the age-related condition comprises increased molecular heterogeneity. In some embodiments, the age-related condition comprises increased functional impairment in a tissue. In some embodiments, the expression level of the gene in a skin tissue is increased. In some embodiments, the expression level of the gene in an adipose tissue is increased. In some embodiments, the expression level of the gene in blood is increased. In some embodiments, the expression level of the gene in a neuronal tissue is increased. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for treating an individual in need thereof, comprising: administering to an individual an effective amount of a nitroxide antioxidant to increase the level of expression of the gene associated with the apoptosis pathway. In some embodiments, the methods further comprise: identifying an individual. In some embodiments, the individual has a disease-related decreased expression level of the gene (e.g., a gene associated with the apoptosis pathway). In some embodiments, the disease can be selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the gene is selected from the group consisting of: Cd51, Perp, Unc5b, Bag5 and Bri3. In some embodiments, the human subject is over the age of 35. In some embodiments, the human subject is over the age of 45. In some embodiments, the human subject is over the age of 55. In some embodiments, the human subject is over the age of 65. In some embodiments, the expression level of the gene in a skin tissue is increased. In some embodiments, the expression level of the gene in an adipose tissue is increased. In some embodiments, the expression level of the gene in blood is increased. In some embodiments, the expression level of the gene in a neuronal tissue is increased. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for treating an individual having or at risk of developing a condition due to aging, comprising: administering to an individual an effective amount of a nitroxide antioxidant, whereby the expression level of a gene (e.g., a gene associated with the apoptosis pathway) is increased. In some embodiments, the methods further comprise: identifying the individual. In some embodiments, the individual is over the age of 35. In some embodiments, the individual has a decreased expression level of the gene. In some embodiments, the gene is selected from the group consisting of: Cd51, Perp, Unc5b, Bag5 and Bri3. In some embodiments, the condition is an age-related condition. In some embodiments, the age-related condition comprises increased senescence in a tissue. In some embodiments, the age-related condition comprises inactivation of the apoptosis pathway in a tissue. In some embodiments, the age-related condition comprises increased molecular heterogeneity. In some embodiments, the age-related condition comprises increased functional impairment in a tissue. In some embodiments, the age-related condition is selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the human subject is over the age of 35. In some embodiments, the human subject is over the age of 45. In some embodiments, the human subject is over the age of 55. In some embodiments, the human subject is over the age of 65.

Disclosed herein are methods for treating an individual having cancer. In some embodiments, the methods comprise: administering to an individual an effective amount of a nitroxide antioxidant (e.g., the nitroxide antioxidant is 4-hydroxy-2,2,6,6-tetramethylpiperidine-1-oxyl), wherein the individual has a cancer whose expression level of Unc5b is downregulated, whereby the expression level of Unc5b is increased. In some embodiments, the methods further comprise: identifying the individual. In some embodiments, the cancer is an age-related cancer. The individual can be over the age of 35 or 55. The cancer can be selected from the group consisting of bladder cancer, colorectal cancer, hepatocellular carcinoma, prostate carcinoma, and kidney carcinoma.

Disclosed herein are methods for treating an individual having an infection. In some embodiments, the methods comprise: administering to an individual an effective amount of a nitroxide antioxidant (e.g., the nitroxide antioxidant is 4-hydroxy-2,2,6,6-tetramethylpiperidine-1-oxyl), wherein the individual has an infection, whereby the expression level of Cd51 is increased. In some embodiments, the methods further comprise: identifying the individual. The infection can be a bacterial infection. The infection can be caused by a gram positive bacterium, or a gram negative bacterium. The infection can be caused by bacterium of the genus *Mycobacterium* (e.g., *Mycobacterium tuberculosis*). The infection can be a *Mycobacterium avium intracellulare* infection. The infection can be caused by a bacterium of the genus *Corynebacterium*, e.g. *Corynebacterium parvum*. The infection can be caused by a bacterium of the genus *Listeria*, e.g., *Listeria monocytogenes*. The infection can be caused by a bacterium of the genus *Streptococci*. The infection can result in sepsis, meningitis, or a combination thereof. The infection can be a fungal infection. The infection can be a viral infection. The individual can have a compromised immune system. The compromised immune system can be age related. The individual can be over the age of 35 or 55. The increased expression level of Cd51 can inhibit apoptosis of immune cells. The immune cells can comprise macrophages or T-cells. The methods can further comprise inhibiting or delaying development of the infection.

Disclosed herein are methods for treating an individual having a neurodegenerative disease. In some embodiments, the methods comprise: administering to an individual an effective amount of a nitroxide antioxidant (e.g., the nitroxide antioxidant is 4-hydroxy-2,2,6,6-tetramethylpiperidine-1-oxyl), wherein the individual has a neurodegenerative disease whose expression level of Bag5 is downregulated, whereby the expression level of Bag5 is increased. In some embodiments, the methods further comprise: identifying the individual. The neurodegenerative disease can be Alzheimer's disease, Parkinson's disease, Huntington's disease, amyotrophic lateral sclerosis, or a combination thereof. The neurodegenerative disease can result in spinal ataxis, spinocerebellar degenerations, or a combination thereof. The neurodegenerative disease can be an age-related neurodegenerative disease. The individual can be over the age of 35 or 55. The individual can be over the age of 55. The expression level of Bag5 can be increased in a neuronal tissue. In some embodiments, the methods further comprise: inhibiting or delaying development of the neurodegenerative disease.

Some embodiments disclosed herein provide a method for inhibiting deposition of amyloid plaque, comprising: administering to an individual known or suspected to have a decreased expression level of Bri3 an effective amount of a nitroxide antioxidant, whereby an expression level of Bri3 is increased, and whereby the increased expression level of Bri3 inhibits amyloid protein processing. In some embodiments, the individual has not been diagnosed with an amyloid-plaque-related disease. In some embodiments, said inhibition of amyloid protein processing inhibits cleavage of beta amyloid. In some embodiments, the neurodegenerative disease is Alzheimer's Disease. In some embodiments, amyloid plaque formation results in a cardiovascular disease. In some embodiments, the nitroxide antioxidant is 4-hydroxy-2,2,6,6-tetramethlpiperidine-1-oxyl. The individual can be known to have the decreased expression level of Bri3. The individual can be suspected to have the decreased expression level of Bri3. The increased expression of Bri3 can inhibit amyloid precursor protein processing thereby inhibiting amyloid plaque deposition. The method can further comprise selecting the individual by either monitoring Bri3 expression over time, or by identifying the presence of one or more risk factors associated with falling Bri3 expression, or both, wherein the risk factors are selected from the individual's age, family history, health conditions, medical history, or habits.

Some embodiments disclosed herein provide methods for inhibiting development of Alzheimer's disease, comprising: administering to an individual known to have a decreased expression level of Bri3 an effective amount of a nitroxide antioxidant (e.g., 4-hydroxy-2,2,6,6-tetramethylpiperidine-1-oxyl), whereby an expression level of Bri3 is increased, and whereby the increased expression level of Bri3 inhibits amyloid protein processing. In some embodiments, the inhibition of amyloid protein processing inhibits beta amyloid mediated plaque formation. In some embodiments, said Alzheimer's Disease is defined by amyloid plaque formation. In some embodiments, inhibition of amyloid protein processing inhibits cleavage of beta amyloid.

Some embodiments disclosed herein provide a method for inhibiting deposition of beta amyloid, comprising: identifying an individual having Alzheimer's Disease, wherein the Alzheimer's disease is characterized by deposition of beta amyloid plaque, and wherein the individual is known to have a reduced level of Bri3 expression; and administering to the individual an amount of a nitroxide antioxidant effective to increase expression levels of Bri3, whereby deposition of beta amyloid plaque is inhibited. In some embodiments, inhibition of amyloid protein processing inhibits cleavage of beta amyloid. The increased Bri3 expression can inhibit amyloid precursor protein processing thereby reducing cleavage of beta amyloid and delaying development of Alzheimer's disease. The increased Bri3 expression can suppress development of Alzheimer's disease. The nitroxide antioxidant can be 4-hydroxy-2,2,6,6-tetramethlpiperidine-1-oxyl.

Some embodiments disclosed herein provide a method of inhibiting amyloid plaque deposition in an individual known or suspected to exhibit falling levels of Bri3 expression, comprising: selecting the individual by either monitoring Bri3 expression over time, or by identifying the presence of one or more risk factors associated with falling Bri3 expression, or both, wherein the risk factors are selected from the individual's age, family history, health conditions, medical history, or habits; and administering a nitroxide antioxidant to the selected individual in an amount sufficient to increase Bri3 expression; whereby the increased expression of Bri3 inhibits amyloid precursor protein processing thereby inhibiting amyloid plaque deposition.

Disclosed herein are embodiments of a method of suppressing development of Alzheimer's disease in an individual in need thereof, the method comprising: administering to the individual an amount of a nitroxide antioxidant effective to increase Bri3 expression, wherein the increased Bri3 expression inhibits amyloid precursor protein processing thereby reducing cleavage of beta amyloid and delaying development of Alzheimer's disease. The Alzheimer's disease can be characterized by deposition of beta amyloid plaque. The individual can be known to have a reduced level of Bri3 expression. The nitroxide antioxidant can 4-hydroxy-2,2,6,6-tetramethlpiperidine-1-oxyl.

DETAILED DESCRIPTION

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). For purposes of the present disclosure, the following terms are defined below.

All patents, applications, published applications and other publications referred to herein are incorporated by reference for the referenced material and in their entireties. If a term or phrase is used herein in a way that is contrary to or otherwise inconsistent with a definition set forth in the patents, applications, published applications and other publications that are herein incorporated by reference, the use herein prevails over the definition that is incorporated herein by reference.

As used herein, the term "expression" means the detection of a gene product that is expressed or produced by a nucleic acid molecule by standard molecular biology methods, which gene product refers to e.g. an unspliced RNA, an mRNA, a splice variant mRNA, a polypeptide, a post-translationally modified polypeptide, a splice variant polypeptide etc., and specifically products made using an RNA gene product as a template, e.g. cDNA of the RNA.

As used herein, "differential expression" of a gene means that the expression of the gene is at a higher level ("increased expression") or lower level ("decreased expression") in a human subject suffering from a disease, for example cancers and autoimmune diseases, relative to its expression in a normal or control subject. Differential expression includes both quantitative, as well as qualitative, differences in the temporal or cellular expression pattern in a gene or its expression products among, for example, normal and diseased cells, or among cells which have undergone different disease events or disease stages.

As used herein, "increasing the expression level" of a gene means causing the expression of the gene to increase by treating the human subject with a compound, for example a nitroxide antioxidant, such that the expression level of the gene after treatment is higher than the expression level of the gene before treatment in the human subject.

It is understood that aspects and embodiments of the invention described herein include "consisting" and/or "consisting essentially of" aspects and embodiments.

Other objects, advantages and features of the present invention will become apparent from the following specification taken in conjunction with the accompanying drawings.

Human Subject Identification

The present disclosure relates to methods of treating alteration in gene expression (e.g., age-related or non-age-related alteration). It has been shown that the expression level of a number of genes, such as ones playing important roles in cell growth and apoptosis regulation, is decreased or downregulated in aging human beings (Glass et al. Genome Biology 2013, 14:R75, the content of which is hereby incorporated by reference in its entirety). Gene expression changes also play important roles in aging and serve as biomarkers of physiological decline and disease conditions, such as Alzheimer's disease. Decreased gene expression levels, due to accumulation of DNA damages, were observed in the human brain (Lu et al. Nature 429, 883-891 (24 June 2004), the content of which is hereby incorporated by reference in its entirety).

Therefore, disclosed herein are methods of treating a human subject having an age-related decrease or downregulation in gene expression levels, such as those genes associated with the apoptosis pathway. In some embodiments, the human subject can be identified based on the human subject's age, gene expression level, family history, health conditions, medical history, habits, or a combination thereof.

Regardless of the cause of the downregulation, some common terminology can be used. In some embodiments, the expression level of a gene (such as Cd51, Perp, Unc5b, Bag5 or Bri3) in a human subject is considered to be downregulated or decreased if the decrease in the expression level of that gene is statistically significant compared to that of a control or a reference. The control or reference can be, for example, a normal healthy population, a population at large, a collection of individuals of the same age or condition or sex, or the same human subject at a different time (e.g., at an earlier time of life when the human subject does not have the disease or condition that results in the downregulation).

In some embodiments, a normal healthy population or a population at large can be a population having the same or similar gender, age, and/or race, compared to the human subject. In some embodiments, the expression level of the gene in the control or reference can be the mean or median expression level of the gene in control subjects in the control or reference subjects in the reference. The decrease in expression level can be statistically significant if the probability of the observed difference occurring not by chance, the confidence level, is greater than a threshold. The threshold can be, or be about, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9%, or a number or a range between any two of these values.

In some embodiments, the decrease in expression level can be, or be about, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 20%, 30%, 40%, 50%, 60%, 70%, 80%, 90%, 100%, or a number or a range between any two of these values. In some embodiments, the decrease in expression level can be at least 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 20%, 30%, 40%, 50%, 60%, 70%, 80%, 90%, 100%, or more.

In some embodiments, the human subject may have an age that is, is about, is over 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 years old.

In some embodiments, the human subject is identified based on the human subject's expression profiles of one or more genes associated with the apoptosis pathway. Non-limiting exemplary methods for determining the human subject's expression profiles include: amplification techniques such as PCR and RT-PCR (including quantitative variants), hybridization techniques such as in situ hybridization, microarrays, blots, and others, and high throughput sequencing techniques like Next Generation Sequencing (lllumina, Roche Sequencer, Life Technologies SOLID™), Single Molecule Real Time Sequencing (Pacific Biosciences), True Single Molecule Sequencing (Helicos), or sequencing methods using no light emitting technologies but other physical methods to detect the sequencing reaction or the sequencing product, like Ion Torrent (Life Technologies). Non-limiting exemplary methods for determining the human subject's expression profiles include: binding techniques such as ELISA, immunohistochemistry, microarray and functional techniques such as enzymatic assays.

Genes of Interests

In some embodiments, administering to the human subject the effective amount of the nitroxide antioxidant results in an increased expression level of a gene, for example a gene associated with the apoptosis pathway. Therefore, some embodiments disclosed herein provide methods for treating an individual in need thereof, comprising administering to an individual an effective amount of a nitroxide antioxidant to increase the level of expression of a gene (e.g., a gene associated with the apoptosis pathway). In some embodiments, the methods further comprise: identifying the individual. In some embodiments, the individual has a disease-related decreased expression level of the gene (e.g., a gene associated with the apoptosis pathway). Some embodiments disclosed herein provide methods for treating an individual in need thereof, comprising administering to an individual an effective amount of a nitroxide antioxidant to increase the level of expression of a gene (e.g., a gene associated with the apoptosis pathway). In some embodiments, the methods further comprise: identifying the individual. In some embodiments, the individual is in need of an increased expression level of the gene (e.g., a gene associated with the apoptosis pathway).

Non-limiting examples of diseases associated with altered level of apoptosis include cancer; breast cancer; lung cancer; kidney cancer; cancers of the ovary and uterus; cancer of the central nervous system; cancers of the head and neck; melanoma; lymphomas; leukemia; neurological disorders; Alzheimer's disease; Parkinson's disease; Huntington's disease; amyotrophic lateral sclerosis; stroke; cardiovascular disorders; ischemia; heart failure; infectious diseases; bacterial infections; viral infections; autoimmune diseases; systemic lupus erythematosus; autoimmune lymphoproliferative syndrome; rheumatoid arthritis; and thyroiditis.

Non-limiting exemplary genes involved in the apoptosis pathway include those involved in the extrinsic apoptosis pathway (FAS, FASLG, TNFRSF10A, TNFRSF10B, TNFRSF10C, TNFRSF10D, TNFRSF11B, TNFSF10, TNFRSF1A, TNF, FADD, CFLAR), those in the Caspases family (CASP1, CASP2, CASP3, CASP4, CASP5, CASP6, CASP7, CASP8, CASP9, CASP10, CASP14), those in the IAPs family (NAIP, BIRC2, BIRC3, XIAP, MRCS, BIRC6, BIRC7), those involved in the mitochondrial/intrinsic apoptosis pathway (Bcl-2 family: BCL2, MCL1, BCL2L1, BCL2L2, BCL2A1, BCL2L10, BAX, BAK1, BOK, BID, BCL2L11, BMF, BAD, BIK, HRK, PMAIP1, BNIP3, BNIP3L, BCL2L14, BBC3, BCL2L12, and BCL2L13; and other proteins: APAF1, CYCS, DIABLO, HTRA2, AIFM1, and ENDOG).

The gene associated with the apoptosis pathway can be Cd51, Perp, Unc5b, Bag5 or Bri3. For example, the treatment can result in increased expression levels of Cd51, Perp, Unc5b, Bag5, Bri3, or any combination thereof. The increased expression levels of Cd51, Perp, Unc5b, Bag5, Bri3, or any combination thereof, can increase the level of apoptosis. The increased level of apoptosis can result in a decrease in or disappearance of signs and symptoms of a disease associated with decreased apoptosis, including the curing of the disease associated with decreased apoptosis. In some embodiments, the increased expression levels of Cd51, Perp, Unc5b, Bag5, Bri3, or any combination thereof, can decrease the level of apoptosis. The decreased level of apoptosis can result in a decrease in or disappearance of signs and symptoms of the disease associated with increased apoptosis, including the curing of the disease associated with increased apoptosis.

Cd51

Cd51 is also known as apoptosis inhibitor of macrophage (AIM), Spα, and apoptosis inhibitor 6. Higher Cd51 levels have been observed in younger people, especially in women (Yamazaki et al., PLoS One. (2014) 9(10):e109123, the content of which is incorporated by reference in its entirety). Thus, estrogen can be involved in the increase in circulating Cd51 levels. Consequently, up-regulation of Cd51 by, for example, a nitroxide antioxidant can prevent and counteract age-related diseases caused by lower Cd51 levels.

Cd51 participates in macrophage homeostasis, including macrophage survival by inhibiting apoptosis. Macrophages play a major role in host innate defense. They can be found in tissues, for example, that function in the filtration of blood or lymph fluids, including liver, spleen, lung, and lymph nodes. Macrophages recognize, internalize, and destroy endogenous and foreign substances that may be harmful. Inflammation is a major mechanism to protect organisms from damage in responding to pathogen infection and tissue injury.

Cd51 is an immune regulator that inhibits immune cell apoptosis at the inflammatory sites and functions as a modulator in immune response. Cd51 has been shown to be involved in pattern recognition of bacteria and in the modulation of monocyte inflammatory responses (Sarrias et al., J. Biol. Chem. (2005) 280:35391-35398, the content of which is incorporated by reference in its entirety). Cd51 has been shown to potentiate the antimicrobial response against *Mycobacterium tuberculosis* by enhancing autophagy (Sanjurjo et al., LoS One. (2013) 8(11):e79670, the content of which is incorporated by reference in its entirety). Cd51 has been shown to inhibit apoptosis of T cells and natural killer T (NKT) cells from *Corynebacterium parvum*-induced liver granulomas (Kuwata et al., Comp. Hepatol. (2004) 3, Suppl. 1:S44, the content of which is incorporated by reference in its entirety). Cd51 has been shown to prevent apoptosis of $CD4^+CD8^+$ (CD4/CD8) double-positive thymocytes induced by dexamethasone and γ-irradiation awaiting maturation in the thymus (Miyazaki et al., J. Exp. Med. (1999) 189:413-422, the content of which is incorporated by reference in its entirety).

Furthermore, Cd51 has been shown to support the survival and the phagocytic activity of macrophages in liver inflammatory (hepatitis) lesions (Haruta et al., J. Biol. Chem. (2001) 276:22910-22914, the content of which is incorporated by reference in its entirety). Cd51 has been shown to be responsible for the resistance to infection with the intracellular bacteria *Listeria monocytogenes* and macrophage survival and bacterial clearance in *L. monocytogenes* infection (Joseph et al. Cell (2004) 119:299-309, the content of which is incorporated by reference in its entirety). Cd51 has been shown to mediate protection of macrophages from the apoptotic effects of oxidized lipids, including oxidized low density lipoprotein (oxLDL). Cd51 has been shown to facilitate cellular adhesion, promotion of lipid accumulation through enhanced CD36-mediated uptake of oxLDL, and macrophage survival within atherosclerotic lesions (Arai et al., Cell Metab. (2005) 1:201-213; Amézaga et al., J. Leukoc. Biol. (2014) 95(3):509-20, the contents of which are incorporated by reference in their entireties). Consequently, up-regulation of Cd51 inhibits immune cell apoptosis and strengthens innate immune response, for example, at lesion sites. And increasing the expression level of Cd51 can be used to treat a human subject with an age-related disease caused by a decreased expression level of Cd51, a human subject having a decreased expression of Cd51, or any combination thereof Perp Perp is an important mediator of stratified epithelial development, cell adhesion, and apoptosis through desmosomal activities. Perp has been shown to be a p53 transcriptional target pro-apoptotic gene expressed in high levels during apoptosis (Ihrie et al., Current Biology (2003) 13(22):1985-1990; Nowak et al., Cell Death and Differentiation (2005) 12(1):52-64, the contents of which are incorporated by reference in their entireties). Perp has been shown to contribute to radiation-induced apoptosis in $CD4^+$ $CD8^+$ thymocytes which undergo p53-dependent apoptotic response (Ihrie et al., Current Biology (2003) 13(22):1985-1990; Lowe et al., Nature (1993) 362(6423):847-849, the contents of which are incorporated by reference in their entireties). Perp induction has been linked to p53-dependent apoptosis, and Perp has been shown to be an effector of p53-dependent apoptosis (Attardi et al., Genes Dev. (2000) 14(6):704-18, the content of which is incorporated by reference in its entirety). Perp has been observed to lead to an enhanced activity of the second mitochondria-derived activator of caspase (Smac) cascade (Chen et al., Cancer Biol. Ther. (2011) 12(12):1114-9, the content of which is incorporated by reference in its entirety). Smac promotes caspases-9 activation. Caspase-9 is an initiator caspase, and is activated and required during apoptosis. Thus, increasing the expression level of Perp can increase apoptosis in a human subject with an insufficient level of apoptosis, possibly caused by a decreased expression of Perp. Increasing the expression level of Perp can increase the expression level of Perp in a human subject who needs an increased expression level of Perp, for example, a human subject having a disease-related decreased expression level of Perp.

Perp has been shown to be required for Salmonella-induced inflammation (Hallstrom et al., Cell Microbiol. (2015) 17(6):843-59, the content of which is incorporated by reference in its entirety). Perp has been linked to human longevity (Flachsbart et al., Mutat. Res. (2010) 694(1-2):13-9, the content of which is incorporated by reference in its entirety). Thus, increasing the expression level of Perp can be used to treat a human subject with an age-related disease caused by a decreased expression level of Perp, a human subject having a decreased expression of Perp, or any combination thereof.

Perp is a putative tumor suppressor gene and is downregulated in metastasizing cells, mammary carcinoma cells, and tumor tissues (Hildebrandt et al., Anticancer Res. (2000) 20(5A):2801-9, the content of which is incorporated by reference in its entirety). Downregulation of Perp has been reported in tumors of the ovary, uterus and breast, and in cutaneous melanoma, pancreas and mammary carcinoma cell lines, compared with the respective normal tissues and non-metastasizing cell lines. Loss of heterozygosity for Perp has been shown in cell lines derived from melanoma, breast, pancreas, cervical, prostate and colon carcinoma. Perp has been shown to be significantly downregulated in aggressive monosomy-3 type primary uveal melanoma (UM) tumors, compared to less aggressive disomy-3 type (Davies et al., J. Cell .Mol. Med. (2009) 13:1995-2007; Paraoan et al, Exp. Eye. Res. (2006) 83(4):911-9, the contents of which are incorporated by reference in their entireties). Perp expression has been shown to stabilize active p53, thus p53-regulated apoptosis, via modulation of p53-MDM2 interaction in uveal melanoma cells (Davies et al., Cell Death and Disease (2011) 2:e136, the content of which is incorporated by reference in its entirety).

Deficiency of Perp has been shown to alter mammary gland homeostasis and promote cancer (Dusek et al., Breast Cancer Res. (2012) 14(2):R65, the content of which is incorporated by reference in its entirety). Loss of Perp has been shown to promote tumorigenesis (Beaudry et al., PLoS Genet. (2010) 6(10): e1001168, the content of which is incorporated by reference in its entirety). For example, Perp is a tumor suppressor of skin cancer. The lack of Perp has been shown to impair cell adhesion as a result of aberrant desmosome assembly, thereby diminishing tumor development (Marques et al., Cancer Res. (2005) 65:6551-6, the content of which is incorporated by reference in its entirety).

Squamous cell carcinoma (SCC) is a malignant proliferation of the keratinocyte of the epidermis. Perp has been reported to be downregulated during SCC progression, and Perp deficiency has been reported to promote SCC (Beaudry et al., PLoS Genet. (2010) 6(10): e1001168, the content of which is incorporated by reference in its entirety). The loss of Perp expression has been reported to correlate with the progression of oral cavity SCC with increased local relapse (Kong et al., Oral Surg. Oral Med. Oral Pathol. Oral Radiol. (2013) 115(1):95-103, the content of which is incorporated by reference in its entirety). Thus, increasing the expression level of Perp can be used to treat a human subject with cancer such as SCC or oral cavity SCC.

Perp has been shown to be a target of the p53-related transcription factor, p63, involved in maintaining epithelial integrity by promoting desmosomal cell-cell adhesion (Ihrie et al., Cell (2005) 120(6):843-56, the content of which is incorporated by reference in its entirety). Lack of Perp can result in postnatal lethality accompanied by dramatic blisters throughout their stratified epithelia, including the oral mucosa and skin, possibly because of a reduction in desmosome number and compromised desmosome complex formation. Thus, Perp is a critical component of the desmosome in the skin and other stratified epithelia.

Decreased Perp expression level has been shown in peripheral blood mononuclear cells from human subjects with rheumatoid arthritis, and this decreased expression Perp expression negatively correlates with severity and progression of rheumatoid arthritis (Du et al., Clinical and Developmental Immunology (2013) 2013:256462, the content of which is incorporated by reference in its entirety). And Perp may prohibit rheumatoid arthritis by regulating interleukin (IL)-17, which participates in the inflammatory process and disease activity of rheumatoid arthritis (Kohno et al., Modern Rheumatology (2008) 18(1):15-22, the content of which is incorporated by reference in its entirety). Loss of Perp has been shown to enhance the phenotypic effects of pemphigus vulgaris, an autoimmune bullous disease in which autoantibodies against proteins of the desmosomal adhesion complex perturb desmosomal function, leading to intercellular adhesion defects in the oral mucosa and skin (Nguyen et al., J. Invest. Dermatol. (2009) 129(7): 1710-8, the content of which is incorporated by reference in its entirety). Thus, increasing the expression level of Perp can be used to treat a human subject with an autoimmune disease such as rheumatoid arthritis.

Unc5b

Unc5b is also known as Unc5h2. Down-regulation of Unc5b has been shown to significantly inhibit apoptosis (He et al., Mol. Biol. Cell. (2011) 22(11):1943-54, the content of which is incorporated by reference in its entirety). Thus, increasing the expression level of Unc5b can increase apoptosis in a human subject with an insufficient level of apoptosis, possibly caused by a decreased expression of Unc5b. Increasing the expression level of Unc5b can increase the expression level of Unc5b in a human subject who needs an increased expression level of Unc5b, for example, a human subject having a disease-related decrease in the expression level of Unc5b.

The expression of Unc5b has been shown to be down-regulated in multiple cancers, including colorectal, breast, ovary, uterus, stomach, lung, and kidney cancers (Thiebault et al., Proc. Natl. Acad. Sci. U.S.A. (2003) 100(7):4173-8, the content of which is incorporated by reference in its entirety). Unc5b has been shown to mediate p53-dependent apoptosis through death-associated protein kinase (DAP-kinase) (Llambi et al., EMBO J. (2005) 24(6):1192-201; Arakawa, Cell Death Differ. (2005) 12(8):1057-65, the contents of which are incorporated by reference in their entireties). Up-regulation of Unc5b has been reported to be associated with the antimelanoma effect of IFN-gamma (Gollob et al., Cancer Res. (2005) 65(19):8869-77, the content of which is incorporated by reference in its entirety).

Decreased Unc5b expression has been observed in bladder cancer cells (Liu et al., BMC Cancer. (2014) 14: 93, the content of which is incorporated by reference in its entirety). Decreased Unc5b expression has been shown in prostate carcinoma cells (Kong et al., Tumour Biol. (2013) 34(5): 2765-72, the content of which is incorporated by reference in its entirety). It has been shown that Unc5b emerged more in bladder cancer cells with lower degrees of malignancy than those with higher degrees of malignancy; Unc5b expression in bladder cancer cells was significantly reduced compared to normal bladder cells, and low Unc5b expression was an independent risk factor for postoperative recurrence in patients with different stages and grades bladder cancer (Liu et al., Tumour Biol. (2013) 34(4):2099-108, the content of which is incorporated by reference in its entirety). Unc5b mRNA has been shown to be down-expressed in bladder cancer tissues. Furthermore, human subjects with lower Unc5b expression in tumors have been shown to have significantly higher recurrence rate after curative surgery and poorer prognosis than those with higher Unc5b expression. Unc5b has been shown to be downregulated in kidney carcinoma (Zhan et al., Tumour Biol. (2013) 34(3):1759-66, the content of which is incorporated by reference in its entirety).

Further, Unc5b mRNA expression has been shown to decrease in some colorectal cancer human subjects, and the human subjects with low-Unc5b-expression tumors showed a significantly higher recurrence rate after curative surgery (Okazaki et al., Int. J. Oncol. (2012) 40(1):209-16, the content of which is incorporated by reference in its entirety). Thus, increasing the expression level of Unc5b can be used to treat a human subject with cancer.

Bag5

Bag5 has been shown to function as the nucleotide exchange factor of Hsp70 for the enhancement of protein refolding (Arakawa et al. Structure (2010) 18(3):309-19, the content of which is incorporated by reference in its entirety). Bag5 has been shown to directly interacted with mutations in PTEN-induced kinase 1 (PINK1), and regulated PINK1 degradation via ubiquitin proteasome system (UPS) (Wang et al., PLoS One. (2014) 9(1):e86276, the content of which is incorporated by reference in its entirety). Loss of the stability of PINK1 may contribute to sporadic Parkinson's disease (PD). Bag5 has been reported to protect mitochondria against MPP+− and rotenone-induced oxidative stress. Thus, increasing the expression level of Bag5 can be used to treat a human subject with an age-related disease caused by a decreased expression level of Bag5, a human subject having a decreased expression of Bag5, or any combination thereof.

Bag5 has been reported to be linked to non-Hodgkin lymphoma (Kelly et al., Cancer Epidemiol. Biomarkers. Prey. (2010) 19(11):2847-2858, the content of which is incorporated by reference in its entirety). Thus, increasing the expression level of Bag5 can be used to treat a human subject with cancer such as non-Hodgkin lymphoma.

Bri3

Increasing the expression level of Bri3 in a human subject in needs thereof may be desirable, for example, a human subject having a disease-related decreased expression level of Bri3.

Reducing Bri3 expression has been shown to increase beta-amyloid (referred to in various literature references, and in this application, as beta-amyloid, β-amyloid, βA, amyloid-beta, Abeta, and/or Aβ) secretion (Matsuda et al, J. Biol. Chem. (2009) 284(23):15815-25, the content of which is incorporated by reference in its entirety). βA is the main component of the amyloid plaques found in the brains of Alzheimer patients. Bri3 has been shown to interact with amyloid precursor protein (APP) and inhibits APP processing (Matsuda et al., J. Biol. Chem. (2005) 280(32):28912-6; Matsuda et al., J. Neurosci. (2008) 28(35):8668-76; Fotinopoulou et al., J. Biol. Chem. (2005) 280(35):30768-72, the contents of which are incorporated by reference in their entireties). Specifically, Bri3 overexpression reduces both α- and β-amyloid precursor protein (αAPP and βAPP) cleavage and formation of βA. Thus, Bri3 expression or overexpression can reduce βAPP cleavage into βA. Reduced βAPP cleavage into βA can inhibit or reduce amyloid plaque deposition. Reducing amyloid plaque deposition can inhibit, suppress, prevent, or reverse AD or symptoms related to AD. Furthermore, Bri3 does not cause the massive accumulation of cleaved APP C-terminal fragment in some subjects (Matsuda et al).

In Alzheimer's disease (AD), the amyloidogenic pathway generating βA starts by β-secretase cleavage of β-amyloid precursor protein (βAPP) at the $EVKM^{652}\downarrow DA$ sequence. Bri3 and BACE1 co-immunoprecipitate and co-localize in neurons from normal human and mouse brain. Furthermore, similar results were seen in human samples from patients with AD and in brains from a mouse model of the disease. (Wickham, L., et al. (2005), β-Amyloid protein converting enzyme 1 and brain-specific type II membrane protein $BRI_3$: binding partners processed by furin. Journal of Neurochemistry, 92:93-102. doi:10.1111/j.1471-4159.2004.02840.x, the content of which is incorporated by reference in its entirety). Bri3 expression is inversely related to APP cleavage to βA (and thereby to amyloid plaque deposition).

Disclosed herein is a method of inhibiting amyloid plaque deposition in an individual, either known or suspected to exhibit falling levels of Bri3 expression, by administering an agent known to increase Bri3 expression. In one embodiment, the method comprises selecting the individual by monitoring Bri3 expression over time thereby confirming that the levels of Bri3 expression are indeed decreasing. In another embodiment, the method comprises selecting the individual by identifying the presence of one or more risk factors associated with amyloid plaque deposition and consequently decreased Bri3 expression; the risk factors may be selected from the individual's age, family history, health conditions, medical history, or habits In some embodiments, the method comprises selecting the individual both by monitoring Bri3 expression over time, and by identifying one or more risk factors. In certain embodiments, the agent known to increase Bri3 expression is a nitroxide antioxidant, and more particularly, in some embodiments, the agent is Tempol. Consequently, by administering an agent known to increase Bri3 expression, the method can inhibit amyloid plaque deposition in the individual known or suspected to exhibit falling levels of Bri3 expression—by inhibiting amyloid precursor protein processing, leading to decreased production and deposition of βA.

Cardiovascular disease (CVD) and Alzheimer disease (AD) are 2 major causes of morbidity and mortality and represent formidable medical and societal challenges. The classical pathological signature of AD is the deposition of amyloid-rich plaques in the brain. βA is a key constituent of these plaques, and its deposition in the brain has been strongly implicated in the pathogenesis of AD. βA proteins are generated from βAPP, a trans-membrane glycoprotein that is sequentially processed by beta- and gamma-secretases to release βA proteins. These βA proteins are hydrophobic monomers, consisting of 39 to 42 amino acids, the most common of which are βA40 and βA42. βA proteins circulate in the plasma and cerebrospinal fluid, βA40 being the most abundant. The longer form, βA42, is most abundant in the classic cerebral plaques of AD, whereas βA40 is the more abundant form in the vascular wall and in platelets. (B. Williams, Amyloid Beta and Cardiovascular Disease. Journal of the American College of Cardiology March 2015, 65 (9) 917-919; DOI: 10.1016/j.jacc.2015.01.013, the content of which is incorporated by reference in its entirety).

Bri3 has been shown to exhibit the ability to stabilize the microtubule network and attenuate the microtubule-destabilizing activity of SCG10 (Gong et al., BMB Rep. (2008) 41(4):287-93, the content of which is incorporated by reference in its entirety). Thus, Bri3 is a critical component of the desmosome in the skin and other stratified epithelia.

Overexpression of Bri3 has been reported to induce apoptosis, possibly through lysosome (Wu et al., Biochem. Biophys. Res. Commun. (2003) 311(2):518-24, the content of which is incorporated by reference in its entirety). Bri3 has also been reported to be down-regulated with colorectal cancer progression (Bandrés et al., Oncology Reports (2007) 17(5):1089-1094, the content of which is incorporated by reference in its entirety). Thus, increasing the expression level of Bri3 can be used to treat a human subject with cancer.

Methods for Counteracting Decrease in Gene Expression or Treating a Condition Related to Decrease in Gene Expression Some embodiments disclosed herein provide methods for counteracting decrease in gene expression (e.g., age-related decrease in gene expression) or treating a disease (e.g., an age-related disease), comprising administering to a human subject an effective amount of a nitroxide antioxidant. In some embodiments, the methods further comprise: identifying the human subject (e.g., a human subject over the age of 35). In some embodiments, the human subject has a decreased expression level of one or more genes (e.g., genes associated with the apoptosis pathway or an age-related disease). In some embodiments, the methods comprise determining the expression level of one or more genes (e.g., genes associated with the apoptosis pathway). However, this may not be necessary in some instances, such as where a decreased expression level of one or more genes associated with the apoptosis pathway can be inferred from the human subject's age, family history, health conditions, medical history, habits, or a combination thereof. In some embodiments, the methods disclosed herein may be used to treat a human subject shows no symptoms of an age-related disease, but is at risk of having an age-related disease. Exemplary risk factors for an age-related disease include, but are not limited to, age, family history, health conditions, medical history, habits, or a combination thereof In some embodiments, risk factors for an age-related disease comprise a decreased expression level of one or more genes associated with the apoptosis pathway. Thus, in some embodiments, the methods comprise administering a nitroxide antioxidant to a human subject suspected to have a decreased expression level of one or more genes, or at risk of developing a decreased expression level of one or more genes (e.g., genes associated with the apoptosis pathway or an age-related disease)—but not known to have such a decreased expression level. The suspicion and/or risk may be inferred from the subject's medical history and/or age.

In some embodiments, administering to the human subject an effective amount of the nitroxide antioxidant results in an increased expression level of a gene, for example a gene associated with the apoptosis pathway. The gene associated with the apoptosis pathway can be Cd51, Perp, Unc5b, Bag5 or Bri3. The treatment of the human subject with the effective amount of the nitroxide antioxidant can result in an increased expression level of the gene. For example, the treatment can result in increased expression levels of Cd51, Perp, Unc5b, Bag5, Bri3, or any combination thereof. The increased expression levels of Cd51, Perp, Unc5b, Bag5, Bri3, or any combination thereof, can increase the level of apoptosis. The increased level of apoptosis can result in a decrease in or disappearance of signs and symptoms of an age-related disease associated with decreased apoptosis, including the curing of the age-related disease. In some embodiments, the increased expression levels of Cd51, Perp, Unc5b, Bag5, Bri3, or any combination thereof, can decrease the level of apoptosis. The decreased level of apoptosis can result in a decrease in or disappearance of signs and symptoms of the age-related disease associated with increased apoptosis, including the curing of the disease associated with age-related disease associated with increased apoptosis.

In some embodiments, the levels of Cd51, Perp, Unc5b, Bag5, Bri3, or any combination thereof in the connective tissue, muscle tissue, nervous tissue, or epithelial tissue may change after the nitroxide antioxidant is administered. Non-limiting examples of the connective tissue include dense connective tissue, loose connective tissue, reticular connective tissue, adipose tissue, cartilage, bone, and extracellular matrix. Non-limiting examples of the muscle tissue includes smooth muscle tissue, cardiac muscle tissue, and skeletal muscle tissue. Non-limiting examples of the nervous tissue include neural tissue of the central nervous system, neural tissue of the peripheral nervous system, the brain, spinal cord, cranial nerves, spinal nerves, and motor neurons. Non-limiting examples of the epithelial tissue include squamous epithelium, cuboidal epithelium, columnar epithelium, glandular epithelium, ciliated epithelium, and skin.

Some embodiments disclosed herein provide methods for treating a disease related to aging in a human subject in need thereof, comprising administering to a human subject an effective amount of a nitroxide antioxidant. In some embodiments, the methods further comprise: identifying the human subject. In some embodiments, the human subject is over the age of 35 and has an age-related disease and/or has a decreased expression level of a gene (e.g., a gene associated with the apoptosis pathway). Some embodiments disclosed herein provide methods for treating an individual having or at risk of developing a condition due to aging, comprising: identifying an individual over the age of 35; and administering to the individual an effective amount of a nitroxide antioxidant, whereby the expression level of the gene associated with the apoptosis pathway is increased.

Non-limiting examples of age-related diseases include cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, hypertension.

Methods for Increasing Expression Level of a Gene

Some embodiments disclosed herein provide methods for increasing the expression level of a gene in a human subject in need thereof, comprising administering to a human subject an effective amount of a nitroxide antioxidant. In some embodiments, the methods further comprise: identifying the human subject. In some embodiments, the human subject has a decreased expression level of a gene (e.g., a gene associated with the apoptosis pathway). Some embodiments disclosed herein provide methods for treating a disease associated with a decreased apoptosis in a patient in need thereof, comprising administering to a human subject an effective amount of a nitroxide antioxidant. In some embodiments, the methods further comprise: identifying the human subject. In some embodiments, the human subject has a decreased expression level of a gene (e.g., a gene associated with the apoptosis pathway). The decreased expression level may be age-related, or disease related. In some embodiments, the disease may be cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, hypertension, or any combination thereof. Some embodiments disclosed herein provide methods for treating an individual in need thereof, comprising administering to a human subject an effective amount of a nitroxide antioxidant. In some embodiments, the methods further comprise: identifying the human subject. In some embodiments, the human subject is over the age of 35 and is in need of an increased expression level of the gene (e.g., a gene associated with the apoptosis pathway). In some embodiments, the methods comprise determining the expression level of one or more genes associated with the apoptosis pathway. However, this may not be necessary in some instances, such as where a decreased expression level of one or more genes associated with the apoptosis pathway can be inferred from the human subject's age, family history, health conditions, medical history, habits, or a combination thereof. In some embodiments, the methods disclosed herein may be used to treat a human subject shows no symptoms of a disease associated with a decreased apoptosis, but is at risk of having a disease associated with a decreased apoptosis. Exemplary risk factors for a disease associated with a decreased apoptosis include, but are not limited to, age, family history, health conditions, medical history, habits, or a combination thereof.

In some embodiments, administering to the human subject an effective amount of the nitroxide antioxidant results in an increased expression level of a gene, for example a gene associated with the apoptosis pathway. The gene associated with the apoptosis pathway can be Cd51, Perp, Unc5b, Bag5 or Bri3. The treatment of the human subject with the effective amount of the nitroxide antioxidant can result in an increased expression level of the gene. For example, the treatment can increase the expression levels of Cd51, Perp, Unc5b, Bag5, Bri3, or any combination thereof. The increased expression of the gene counteracts the decrease in the expression level of the gene.

Methods for Treating Cancer

Some embodiments disclosed herein provide methods for treating cancer in a human subject in need thereof, comprising administering to a human subject an effective amount of a nitroxide antioxidant. In some embodiments, the methods further comprise: identifying the human subject. In some embodiments, the human subject has a cancer and is in need of an increased expression level of a gene associated with the apoptosis pathway or a gene selected from a group consisting of Cd51, Perp, Unc5b, Bag5 or Bri3. In some embodiments, the methods disclosed herein may be used to treat a human subject shows no symptoms of cancer, but is at risk of having cancer. Exemplary risk factors for cancer include, but are not limited to, age, family history, health conditions, medical history, habits, or a combination thereof. In some embodiments, risk factors for cancer comprise a decreased expression level of one or more genes associated with the apoptosis pathway.

Non-limiting examples of the methods for identifying a human subject having a cancer include colonoscopy; sigmoidoscopy; and high-sensitivity fecal occult blood tests. In some embodiments, methods for identifying a human subject having a cancer include low-dose helical computed tomography; mammography; and pap test and human papillomavirus (HPV) testing. In some embodiments, methods for identifying a human subject having a cancer include alpha-fetoprotein blood test; breast magnetic resonance imaging (MRI); CA-125 test; clinical breast exams and regular breast self-exams; prostate-specific antigen (PSA) testing; skin exams; transvaginal ultrasound; and virtual colonoscopy. In some embodiments, methods for identifying a human subject having a cancer include barium enema; biopsy; bone marrow aspiration and biopsy; bone scan; breast MM for early detection of breast cancer; breast MM; colonoscopy; computed tomography (CT) scan; digital rectal exam (DRE); blood and platelets testing; bone marrow testing; umbilical cord blood testing; electrocardiogram (EKG) and echocardiogram; endoscopic techniques; fecal occult blood tests; magnetic resonance imaging (MRI); mammography; multi gated acquisition (MUGA) scan; papanicolaou (pap) test; positron emission tomography and computed tomography (PET-CT) scan; sigmoidoscopy; tumor marker tests; ultrasound; upper endoscopy. In some embodiments, methods for identifying a human subject having a cancer include DNA sequencing; detecting presence of single nucleotide polymorphism (SNIP); and detecting the presence of certain protein markers.

In some embodiments, administering to the human subject an effective amount of the nitroxide antioxidant results in an increased expression level of a gene, for example a gene associated with the apoptosis pathway. The gene associated with the apoptosis pathway can be Cd51, Perp, Unc5b, Bag5 or Bri3. The treatment of the human subject with the effective amount of the nitroxide antioxidant can result in an increased expression of the gene. For example, the treatment can result in increased expression levels of Cd51, Perp, Unc5b, Bag5, Bri3, or any combination thereof. The increased expression level of the gene can increase the level of apoptosis. The increased level of apoptosis can result in a decrease in or disappearance of signs and symptoms of the cancer, including the curing of the cancer.

Non-limiting examples of cancer include bladder and other urothelial cancers; breast cancer; cervical cancer; colorectal cancer; endometrial cancer; endometrial cancer; esophageal cancer; liver (hepatocellular) cancer; lung cancer; neuroblastoma cancer; oral cavity and oropharyngeal cancer; ovarian, fallopian tube, and primary peritoneal cancer; prostate cancer; skin cancer; stomach (gastric) cancer; and testicular cancer.

Non-limiting examples of cancer include acute lymphoblastic leukemia, adult; acute myeloid leukemia, adult; adrenocortical carcinoma; aids-related lymphoma; anal cancer; bile duct cancer; bladder cancer; brain tumors, adult; breast cancer; breast cancer and pregnancy; breast cancer, male; carcinoid tumors, gastrointestinal; carcinoma of unknown primary; cervical cancer; chronic lymphocytic leukemia; chronic myelogenous leukemia; chronic myeloproliferative neoplasms; cns lymphoma, primary; colon cancer; endometrial cancer; esophageal cancer; extragonadal germ cell tumors; fallopian tube cancer; gallbladder cancer; gastric cancer; gastrointestinal carcinoid tumors; gastrointestinal stromal tumors; germ cell tumors, extragonadal; germ cell tumors, ovarian; gestational trophoblastic disease; hairy cell leukemia; hepatocellular (liver) cancer, adult primary; histiocytosis, langerhans cell; hodgkin lymphoma, adult; hypopharyngeal cancer; intraocular (eye) melanoma; islet cell tumors, pancreatic neuroendocrine tumors; kaposi sarcoma; kidney (renal cell) cancer; kidney (renal pelvis and ureter, transitional cell) cancer; langerhans cell histiocytosis; laryngeal cancer; leukemia, adult acute lymphoblastic; leukemia, adult acute myeloid; leukemia, chronic lymphocytic; leukemia, chronic myelogenous; leukemia, hairy cell; lip and oral cavity cancer; liver cancer, adult primary; lung cancer, non-small cell; lung cancer, small cell; lymphoma, adult Hodgkin; lymphoma, adult non-hodgkin; lymphoma, aids-related; lymphoma, primary cns; malignant mesothelioma; melanoma; melanoma, intraocular (eye); merkel cell carcinoma; metastatic squamous neck cancer with occult primary; multiple myeloma and other plasma cell neoplasms; mycosis fungoides and the sézary syndrome; myelodysplastic syndromes; myelodysplastic/myeloproliferative neoplasms; myeloproliferative neoplasms, chronic; paranasal sinus and nasal cavity cancer; nasopharyngeal cancer; neck cancer with occult primary, metastatic squamous; non-hodgkin lymphoma, adult; non-small cell lung cancer; oral cavity cancer, lip oropharyngeal cancer; ovarian epithelial cancer; ovarian germ cell tumors; ovarian low malignant potential tumors; pancreatic cancer; pancreatic neuroendocrine tumors (islet cell tumors); pheochromocytoma and paraganglioma; paranasal sinus and nasal cavity cancer; parathyroid cancer; penile cancer; pheochromocytoma and paraganglioma; pituitary tumors; plasma cell neoplasms, multiple myeloma and other; breast cancer and pregnancy; primary peritoneal cancer; prostate cancer; rectal cancer; renal cell cancer; transitional cell renal pelvis and ureter; salivary gland cancer; sarcoma, Kaposi; sarcoma, soft tissue, adult; sarcoma, uterine; mycosis fungoides and the sézary syndrome; skin cancer, melanoma; skin cancer, nonmelanoma; small cell lung cancer; small intestine cancer; stomach (gastric) cancer; testicular cancer; thymoma and thymic carcinoma; thyroid cancer; transitional cell cancer of the renal pelvis and ureter; trophoblastic disease, gestational; carcinoma of unknown primary; urethral cancer; uterine cancer, endometrial; uterine sarcoma; vaginal cancer; and vulvar cancer.

In some embodiments, non-limiting examples of cancer include, but are not limited to, hematologic and solid tumor types such as acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophoblastic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenstrom's macroglobulinemia, testicular tumors, uterine cancer, Wilms' tumor and the like.

Non-limiting examples of the cancer include acute lymphoblastic leukemia, childhood; acute myeloid leukemia/ other myeloid malignancies, childhood; adrenocortical carcinoma, childhood; astrocytomas, childhood; atypical teratoid/rhabdoid tumor, childhood central nervous system; basal cell carcinoma, childhood; bladder cancer, childhood; bone, malignant fibrous histiocytoma of and osteosarcoma; brain and spinal cord tumors overview, childhood; brain stem glioma, childhood; (brain tumor), childhood astrocytomas; (brain tumor), childhood central nervous system atypical teratoid/rhabdoid tumor; (brain tumor), childhood central nervous system embryonal tumors; (brain tumor), childhood central nervous system germ cell tumors; (brain tumor), childhood craniopharyngioma; (brain tumor), childhood ependymoma; breast cancer, childhood; bronchial tumors, childhood; carcinoid tumors, childhood; carcinoma of unknown primary, childhood; cardiac (heart) tumors, childhood; central nervous system atypical teratoid/rhabdoid tumor, childhood; central nervous system embryonal tumors, childhood; central nervous system germ cell tumors, childhood; cervical cancer, childhood; chordoma, childhood; colorectal cancer, childhood; craniopharyngioma, childhood; effects, treatment for childhood cancer, late; embryonal tumors, central nervous system, childhood; ependymoma, childhood; esophageal tumors, childhood; esthesioneuroblastoma, childhood; ewing sarcoma; extracranial germ cell tumors, childhood; gastric (stomach) cancer, childhood; gastrointestinal stromal tumors, childhood; germ cell tumors, childhood central nervous system; germ cell tumors, childhood extracranial; glioma, childhood brain stem; head and neck cancer, childhood; heart tumors, childhood; hematopoietic cell transplantation, childhood; histiocytoma of bone, malignant fibrous and osteosarcoma; histiocytosis, langerhans cell; hodgkin lymphoma, childhood; kidney tumors of childhood, wilms tumor and other; langerhans cell histiocytosis; laryngeal cancer, childhood; late effects of treatment for childhood cancer; leukemia, childhood acute lymphoblastic; leukemia, childhood acute myeloid/other childhood myeloid malignancies; liver cancer, childhood; lung cancer, childhood; lymphoma, childhood Hodgkin; lymphoma, childhood non-Hodgkin; malignant fibrous histiocytoma of bone and osteosarcoma; melanoma, childhood; mesothelioma, childhood; midline tract carcinoma, childhood; multiple endocrine neoplasia, childhood; myeloid leukemia, childhood acute/other childhood myeloid malignancies; nasopharyngeal cancer, childhood; neuroblastoma, childhood; non-hodgkin lymphoma, childhood; oral cancer, childhood; osteosarcoma and malignant fibrous histiocytoma of bone; ovarian cancer, childhood; pancreatic cancer, childhood; papillomatosis, childhood; paraganglioma, childhood; pediatric supportive care; pheochromocytoma, childhood; pleuropulmonary blastoma, childhood; retinoblastoma; rhabdomyosarcoma, childhood; salivary gland cancer, childhood; sarcoma, childhood soft tissue; (sarcoma), ewing sarcoma; (sarcoma), osteosarcoma and malignant fibrous histiocytoma of bone; (sarcoma), childhood rhabdomyosarcoma; (sarcoma) childhood vascular tumors; skin cancer, childhood; spinal cord tumors overview, childhood brain and; squamous cell carcinoma (skin cancer), childhood; stomach (gastric) cancer, childhood; supportive care, pediatric; testicular cancer, childhood; thymoma and thymic carcinoma, childhood; thyroid tumors, childhood; transplantation, childhood hematopoietic; childhood carcinoma of unknown primary; unusual cancers of childhood; vaginal cancer, childhood; vascular tumors, childhood; and wilms tumor and other childhood kidney tumors.

Non-limiting examples of cancer include embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric osteosarcoma, pediatric rhabdoid kidney tumor, pediatric rhabdomyosarcoma, and pediatric T-cell cancers such as lymphoma and skin cancer.

Methods for Treating Autoimmune Diseases

Some embodiments disclosed herein provide methods for treating an autoimmune disease in a human subject in need thereof, comprising administering to the human subject an effective amount of a nitroxide antioxidant. In some embodiments, the methods further comprise: identifying the human subject. In some embodiments, the human subject has a neural degenerative disease and is in need of an increased expression level of a gene associated with the apoptosis pathway or selected from a group consisting of Cd51, Perp, Unc5b, Bag5 or Bri3. In some embodiments, the methods disclosed herein may be used to treat a human subject shows no symptoms of an autoimmune disease, but is at risk of having an autoimmune disease. Exemplary risk factors for an autoimmune disease include, but are not limited to, age, family history, health conditions, medical history, habits, or a combination thereof In some embodiments, risk factors for an autoimmune disease comprise a decreased expression level of one or more genes, such as Cd51, Perp, Unc5b, Bag5 or Bri3.

In some embodiments, the method comprises administering to the human subject an effective amount of the nitroxide antioxidant results in an increased expression level of a gene, for example a gene such as Cd51, Perp, Unc5b, Bag5 or Bri3. The treatment of the human subject with the effective amount of the nitroxide antioxidant can result in an increased expression level of the gene. For example, the treatment can result in increased expression levels of Cd51, Perp, Unc5b, Bag5, Bri3, or any combination thereof. The increased level of gene can result in a decrease in or disappearance of signs and symptoms of the autoimmune disease, including the curing of the autoimmune disease. Alternatively or in addition, the increased expression levels of Cd51, Perp, Unc5b, Bag5, Bri3, or any combination thereof, can increase the level of apoptosis. The increased level of apoptosis can result in a decrease in or disappearance of signs and symptoms of the autoimmune disease, including the curing of the autoimmune disease. In some embodiments, the increased expression levels of Cd51, Perp, Unc5b, Bag5, Bri3, or any combination thereof, can decrease the level of apoptosis. The decreased level of apoptosis can result in a decrease in or disappearance of signs and symptoms of the autoimmune disease, including the curing of the autoimmune disease.

Non-limiting examples of autoimmune diseases include rheumatoid arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schonlein purpura, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia greata, seronegative arthropathy, arthropathy, Reiter's disease, psoriatic arthropathy, ulcerative colitic arthropathy, enteropathic synovitis, chlamydia, yersinia and salmonella associated arthropathy, spondyloarthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondylitis associated lung disease, vasculitic diffuse lung disease, hemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leukopenia, autoimmune neutropaenia, renal disease NOS, glomerulonephritides, microscopic vasculitis of the kidneys, lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjogren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GBS) infection, mental disorders (e.g., depression and schizophrenia), Th2 Type and Th1 Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma). The human antibodies, and antibody portions of the present application can be used to treat humans suffering from autoimmune diseases, in particular those associated with inflammation, including, rheumatoid spondylitis, allergy, autoimmune diabetes, autoimmune uveitis.

Non-limiting examples of autoimmune diseases include acquired immunodeficiency disease syndrome (AIDS), autoimmune lymphoproliferative syndrome, hemolytic anemia, inflammatory diseases, and thrombocytopenia, acute or chronic immune disease associated with organ transplantation, Addison's disease, allergic diseases, alopecia, alopecia areata, atheromatous disease/arteriosclerosis, atherosclerosis, arthritis (including osteoarthritis, juvenile chronic arthritis, septic arthritis, Lyme arthritis, psoriatic arthritis and reactive arthritis), autoimmune bullous disease, abetalipoprotemia, acquired immunodeficiency-related diseases, acute immune disease associated with organ transplantation, acquired acrocyanosis, acute and chronic parasitic or infectious processes, acute pancreatitis, acute renal failure, acute rheumatic fever, acute transverse myelitis, adenocarcinomas, aerial ectopic beats, adult (acute) respiratory distress syndrome, AIDS dementia complex, alcoholic cirrhosis, alcohol-induced liver injury, alcohol-induced hepatitis, allergic conjunctivitis, allergic contact dermatitis, allergic rhinitis, allergy and asthma, allograft rejection, alpha-1-antitrypsin deficiency, Alzheimer's disease, amyotrophic lateral sclerosis, anemia, angina pectoris, ankylosing spondylitis associated lung disease, anterior horn cell degeneration, antibody mediated cytotoxicity, antiphospholipid syndrome, anti-receptor hypersensitivity reactions, aortic and peripheral aneurysms, aortic dissection, arterial hypertension, arteriosclerosis, arteriovenous fistula, arthropathy, asthenia, asthma, ataxia, atopic allergy, atrial fibrillation (sustained or paroxysmal), atrial flutter, atrioventricular block, atrophic autoimmune hypothyroidism, autoimmune haemolytic anaemia, autoimmune hepatitis, type-1 autoimmune hepatitis (classical autoimmune or lupoid hepatitis), autoimmune mediated hypoglycaemia, autoimmune neutropaenia, autoimmune thrombocytopaenia, autoimmune thyroid disease, B cell lymphoma, bone graft rejection, bone marrow transplant (BMT) rejection, bronchiolitis obliterans, bundle branch block, burns, cachexia, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chlamydia, choleosatatis, chronic alcoholism, chronic active hepatitis, chronic fatigue syndrome, chronic immune disease associated with organ transplantation, chronic eosinophilic pneumonia, chronic inflammatory pathologies, chronic mucocutaneous candidiasis, chronic obstructive pulmonary disease (COPD), chronic salicylate intoxication, colorectal common varied immunodeficiency (common variable hypogammaglobulinaemia), conjunctivitis, connective tissue disease associated interstitial lung disease, contact dermatitis, Coombs positive haemolytic anaemia, cor pulmonale, Creutzfeldt-Jakob disease, cryptogenic autoimmune hepatitis, cryptogenic fibrosing alveolitis, culture negative sepsis, cystic fibrosis, cytokine therapy associated disorders, Crohn's disease, dementia pugilistica, demyelinating diseases, dengue hemorrhagic fever, dermatitis, dermatitis scleroderma, dermatologic conditions, dermatomyositis/polymyositis associated lung disease, diabetes, diabetic arteriosclerotic disease, diabetes mellitus, Diffuse Lewy body disease, dilated cardiomyopathy, dilated congestive cardiomyopathy, discoid lupus erythematosus, disorders of the basal ganglia, disseminated intravascular coagulation, Down's Syndrome in middle age, drug-induced interstitial lung disease, drug-induced hepatitis, drug-induced movement disorders induced by drugs which block CNS dopamine, receptors, drug sensitivity, eczema, encephalomyelitis, endocarditis, endocrinopathy, enteropathic synovitis, epiglottitis, Epstein-Barr virus infection, erythromelalgia, extrapyramidal and cerebellar disorders, familial hematophagocytic lymphohistiocytosis, fetal thymus implant rejection, Friedreich's ataxia, functional peripheral arterial disorders, female infertility, fibrosis, fibrotic lung disease, fungal sepsis, gas gangrene, gastric ulcer, giant cell arteritis, glomerular nephritis, glomerulonephritides, Goodpasture's syndrome, goitrous autoimmune hypothyroidism (Hashimoto's disease), gouty arthritis, graft rejection of any organ or tissue, graft versus host disease, gram negative sepsis, gram positive sepsis, granulomas due to intracellular organisms, group B streptococci (GBS) infection, Grave's disease, haemosiderosis associated lung disease, hairy cell leukemia, hairy cell leukemia, Hallerrorden-Spatz disease, Hashimoto's thyroiditis, hay fever, heart transplant rejection, hemachromatosis, hematopoietic malignancies (leukemia and lymphoma), hemolytic anemia, hemolytic uremic syndrome/thrombolytic thrombocytopenic purpura, hemorrhage, Henoch-Schonlein purpura, Hepatitis A, Hepatitis B, Hepatitis C, HIV infection/HIV neuropathy, Hodgkin's disease, hypoparathyroidism, Huntington's chorea, hyperkinetic movement disorders, hypersensitivity reactions, hypersensitivity pneumonitis, hyperthyroidism, hypokinetic movement disorders, hypothalamic-pituitary-adrenal axis evaluation, idiopathic Addison's disease, idiopathic leukopenia, idiopathic pulmonary fibrosis, idiopathic thrombocytopaenia, idiosyncratic liver disease, infantile spinal muscular atrophy, infectious diseases, inflammation of the aorta, inflammatory bowel disease, insulin dependent diabetes mellitus, interstitial pneumonitis, iridocyclitis/uveitis/optic neuritis, ischemia-reperfusion injury, ischemic stroke, juvenile pernicious anaemia, juvenile rheumatoid arthritis, juvenile spinal muscular atrophy, Kaposi's sarcoma, Kawasaki's disease, kidney transplant rejection, legionella, leishmaniasis, leprosy, lesions of the corticospinal system, linear IgA disease, lipidema, liver transplant rejection, Lyme disease, lymphederma, lymphocytic infiltrative lung disease, malaria, male infertility idiopathic or NOS, malignant histiocytosis, malignant melanoma, meningitis, meningococcemia, microscopic vasculitis of the kidneys, migraine headache, mitochondrial multisystem disorder, mixed connective tissue disease, mixed connective tissue disease associated lung disease, monoclonal gammopathy, multiple myeloma, multiple systems degenerations (Mencel Dejerine-Thomas Shi-Drager and Machado-Joseph), myalgic encephalitis/Royal Free Disease, myasthenia gravis, microscopic vasculitis of the kidneys, mycobacterium avium intracellulare, mycobacterium tuberculosis, myelodyplastic syndrome, myocardial infarction, myocardial ischemic disorders, nasopharyngeal carcinoma, neonatal chronic lung disease, nephritis, nephrosis, nephrotic syndrome, neurodegenerative diseases, neurogenic I muscular atrophies, neutropenic fever, Non-alcoholic Steatohepatitis, occlusion of the abdominal aorta and its branches, occlusive arterial disorders, organ transplant rejection, orchitis/epidydimitis, orchitis/vasectomy reversal procedures, organomegaly, osteoarthrosis, osteoporosis, ovarian failure, pancreas transplant rejection, parasitic diseases, parathyroid transplant rejection, Parkinson's disease, pelvic inflammatory disease, pemphigus vulgaris, pemphigus foliaceus, pemphigoid, perennial rhinitis, pericardial disease, peripheral atherlosclerotic disease, peripheral vascular disorders, peritonitis, pernicious anemia, phacogenic uveitis, pneumocystis carinii pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, postinfectious interstitial lung disease, premature ovarian failure, primary biliary cirrhosis, primary sclerosing hepatitis, primary myxoedema, primary pulmonary hypertension, primary sclerosing cholangitis, primary vasculitis, Progressive supranucleo Palsy, psoriasis, psoriasis type 1, psoriasis type 2, psoriatic arthropathy, pulmonary hypertension secondary to connective tissue disease, pulmonary manifestation of polyarteritis nodosa, post-inflammatory interstitial lung disease, radiation fibrosis, radiation therapy, Raynaud's phenomenon and disease, Raynoud's disease, Refsum's disease, regular narrow QRS tachycardia, Reiter's disease, renal disease NOS, renovascular hypertension, reperfusion injury, restrictive cardiomyopathy, rheumatoid arthritis associated interstitial lung disease, rheumatoid spondylitis, sarcoidosis, Schmidt's syndrome, scleroderma, senile chorea, Senile Dementia of Lewy body type, sepsis syndrome, septic shock, seronegative arthropathies, shock, sickle cell anemia, Sjögren's disease associated lung disease, Sjörgren's syndrome, skin allograft rejection, skin changes syndrome, small bowel transplant rejection, sperm autoimmunity, multiple sclerosis (all subtypes), spinal ataxia, spinocerebellar degenerations, spondyloarthropathy, spondyloarthropathy, sporadic, polyglandular deficiency type I sporadic, polyglandular deficiency type II, Still's disease, streptococcal myositis, stroke, structural lesions of the cerebellum, Subacute sclerosing panencephalitis, sympathetic ophthalmia, Syncope, syphilis of the cardiovascular system, systemic anaphylaxis, systemic inflammatory response syndrome, systemic onset juvenile rheumatoid arthritis, systemic lupus erythematosus, systemic lupus erythematosus-associated lung disease, systemic sclerosis, systemic sclerosis-associated interstitial lung disease, T-cell or FAB ALL, Takayasu's disease/arteritis, Telangiectasia, Th2 Type and Th1 Type mediated diseases, thromboangitis obliterans, thrombocytopenia, thyroiditis, toxicity, toxic shock syndrome, transplants, trauma/hemorrhage, type-2 autoimmune hepatitis (anti-LKM antibody hepatitis), type B insulin resistance with acanthosis nigricans, type III hypersensitivity reactions, type IV hypersensitivity, ulcerative colitic arthropathy, ulcerative colitis, unstable angina, uremia, urosepsis, urticaria, uveitis, valvular heart diseases, varicose veins, vasculitis, vasculitic diffuse lung disease, venous diseases, venous thrombosis, ventricular fibrillation, vitiligo acute liver disease, viral and fungal infections, viral encephalitis/aseptic meningitis, viral-associated hemaphagocytic syndrome, Wegener's granulomatosis, Wernicke-Korsakoff syndrome, Wilson's disease, xenograft rejection of any organ or tissue, yersinia and salmonella-associated arthropathy and the like.

Methods for Treating an Infection

Some embodiments disclosed herein provide methods for treating an infection in a human subject in need thereof, comprising administering to a human subject an effective amount of a nitroxide antioxidant. In some embodiments, the methods further comprise: identifying the human subject. In some embodiments, the human subject has an infection and is in need of an increased expression level of a gene associated with the apoptosis pathway or selected from a group consisting of Cd51, Perp, Unc5b, Bag5 or Bri3. In some embodiments, the methods disclosed herein may be used to treat a human subject shows no symptoms of an infection, but is at risk of having an infection. Exemplary risk factors for an infection include, but are not limited to, age, family history, health conditions, medical history, habits, or a combination thereof. In some embodiments, risk factors for an infection comprise a decreased expression level of one or more genes, such as Cd51, Perp, Unc5b, Bag5 or Bri3.

In some embodiments, the method comprises administering to the human subject an effective amount of the nitroxide antioxidant results in an increased expression level of a gene, for example a gene such as Cd51, Perp, Unc5b, Bag5 or Bri3. The treatment of the human subject with the effective amount of the nitroxide antioxidant can result in an increased expression level of the gene. For example, the treatment can result in increased expression levels of Cd51, Perp, Unc5b, Bag5, Bri3, or any combination thereof. The increased level of gene can result in a decrease in or disappearance of signs and symptoms of the infection, including the curing of the infection. Alternatively or in addition, the increased expression levels of Cd51, Perp, Unc5b, Bag5, Bri3, or any combination thereof, can increase the level of apoptosis. The increased level of apoptosis can result in a decrease in or disappearance of signs and symptoms of the infection, including the curing of the infection. In some embodiments, the increased expression levels of Cd51, Perp, Unc5b, Bag5, Bri3, or any combination thereof, can decrease the level of apoptosis. The decreased level of apoptosis can result in a decrease in or disappearance of signs and symptoms of the infection, including the curing of the infection.

In some embodiments, the infection is a bacterial infection, such as a gram positive bacterium or a gram negative bacterium. In some embodiments, the infection is caused by a bacterium of the genus *Mycobacterium*. The bacterium can be *Mycobacterium tuberculosis*. The infection can a *Mycobacterium avium intracellulare* infection. In some embodiments, the infection is caused by a bacterium of the genus *Corynebacterium*. The bacterium can be *Corynebacterium parvum*. In some embodiments, the infection is caused by a bacterium of the genus *Listeria*. The bacterium can be *Listeria monocytogenes*. In some embodiments, the infection is caused by a bacterium of the genus *Streptococci*. In some embodiments, the infection results in sepsis or in meningitis. In some embodiments, the infection is a fungal infection or a viral infection. In some embodiments, the individual has a compromised immune system. The compromised immune system can be age related. The individual can be over the age of 35 or 35. In some embodiments, the increased expression level of Cd51 inhibits apoptosis of immune cells. The immune cells can comprise macrophages or T-cells. In some embodiments, the method inhibiting or delaying development of the infection.

Methods for Treating a Neurodegenerative Disease

Some embodiments disclosed herein provide methods for treating a neural degenerative disease in a human subject in need thereof, comprising administering to a human subject an effective amount of a nitroxide antioxidant. In some embodiments, the methods further comprise: identifying a human subject. In some embodiments, the human subject has a neural degenerative disease and is in need of an increased expression level of a gene associated with the apoptosis pathway or selected from a group consisting of Cd51, Perp, Unc5b, Bag5 or Bri3. In some embodiments, the methods disclosed herein may be used to treat a human subject shows no symptoms of a neural degenerative disease, but is at risk of having a neural degenerative disease. Exemplary risk factors for a neural degenerative disease include, but are not limited to, age, family history, health conditions, medical history, habits, or a combination thereof In some embodiments, risk factors for a neural degenerative disease comprise a decreased expression level of one or more genes, such as Cd51, Perp, Unc5b, Bag5 or Bri3.

In some embodiments, the method comprises administering to the human subject an effective amount of the nitroxide antioxidant results in an increased expression level of a gene, for example a gene such as Cd51, Perp, Unc5b, Bag5 or Bri3. The treatment of the human subject with the effective amount of the nitroxide antioxidant can result in an increased expression level of the gene. For example, the treatment can result in increased expression levels of Cd51, Perp, Unc5b, Bag5, Bri3, or any combination thereof. The increased level of gene can result in a decrease in or disappearance of signs and symptoms of the neural degenerative disease, including the curing of the neural degenerative disease. Alternatively or in addition, the increased expression levels of Cd51, Perp, Unc5b, Bag5, Bri3, or any combination thereof, can increase the level of apoptosis. The increased level of apoptosis can result in a decrease in or disappearance of signs and symptoms of the neural degenerative disease, including the curing of the neural degenerative disease. In some embodiments, the increased expression levels of Cd51, Perp, Unc5b, Bag5, Bri3, or any combination thereof, can decrease the level of apoptosis. The decreased level of apoptosis can result in a decrease in or disappearance of signs and symptoms of the neural degenerative disease, including the curing of the neural degenerative disease.

In some embodiments, the neurodegenerative disease is Alzheimer's disease, Parkinson's disease, Huntington's disease, amyotrophic lateral sclerosis or a combination thereof. The neurodegenerative disease can result in spinal ataxis, spinocerebellar degenerations, or any combination thereof. The neurodegenerative disease cab be an age-related neurodegenerative disease. The individual can be over the age of 35 or 50. The expression level of Bag5 can be increased in a neuronal tissue. In some embodiments, the method further comprises inhibiting or delaying development of the neurodegenerative disease.

Nitroxide Antioxidant

Non-limiting examples of the nitroxide antioxidant include 2-ethyl-2,5,5-trimethyl-3-oxazolidine-1-oxyl (OXANO), 2,2,6, 6-tetramethylpiperidine-1-oxyl (TEMPO), 4-hydroxy-2,2,6,6-tetramethylpiperidine-1-oxyl (TEMPOL), 4-amino-2,2,6, 6-tetramethyl-1-piperidinyloxy (Tempamine), 3-Aminomethyl-PROXYL, 3-Cyano-PROXYL, 3-Carbamoyl-PROXYL, 3-Carboxy-PROXYL, and 4-Oxo-TEMPO. TEMPO can also be substituted, typically in the 4 position, for example, 4-amino, 4-(2-bromoacetamido), 4(ethoxyfluorophosphonyloxy), 4-hydroxy, 4-(2-iodoacetamido), 4-isothiocyanato, 4-maleimido, 4-(4-nitrobenzoyloxyl), 4-phosphonooxy, and the like.

The use of other nitroxide compounds is also contemplated. According to certain embodiments the nitroxide compound can be selected from the following formulas:

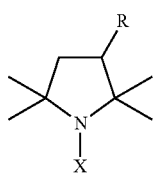

wherein X is selected from O— and OH, and R is selected from COOH, CONH, CN, and CH$_2$NH$_2$;

wherein X is selected from O— and OH, and R$_1$ is selected from CH3 and spirocyclohexyl, and R2 is selected from C2H5 and spirocyclohexyl;

wherein X is selected from O— and OH and R is selected from CONH; and wherein X is selected from O— and OH and R is selected from H, OH, and NH$_2$.

Suitable nitroxide compounds can also be found in Proctor, U.S. Pat. No. 5,352,442, and Mitchell et al., U.S. Pat. No. 5,462,946, both of which are hereby incorporated by reference in their entireties.

Dosage

In some embodiments, the nitroxide antioxidant, non-toxic salts thereof, acid addition salts thereof or hydrates thereof may be administered systemically or locally, usually by oral or parenteral administration. The doses to be administered can be determined depending upon, for example, age, body weight, symptom, the desired therapeutic effect, the route of administration, and the duration of the treatment. In the human adult, the dose per person at a time can be generally from about 0.01 to about 1000 mg, by oral administration, up to several times per day. Specific examples of particular amounts contemplated via oral administration include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000 or more mg. The dose per person at a time can be generally from about 0.01 to about 300 mg/kg via parenteral administration (preferably intravenous administration), from one to four or more times per day. Specific examples of particular amounts contemplated include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300 or more mg/kg. Continuous intravenous administration can also contemplated for from 1 to 24 hours per day to achieve a target concentration from about 0.01 mg/L to about 100 mg/L. Non-limiting examples of particular amounts contemplated via this route include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more mg/L. The dose to be used does can depend upon various conditions, and there may be cases wherein doses lower than or greater than the ranges specified above are used.

Compositions

The nitroxide antioxidant can be administered in the form of, for example, solid compositions, liquid compositions or other compositions for oral administration, injections, liniments or suppositories for parenteral administration.

Solid compositions for oral administration include compressed tablets, pills, capsules, dispersible powders and granules. Capsules include hard capsules and soft capsules. In such solid compositions, Tempol may be admixed with an excipient (e.g. lactose, mannitol, glucose, microcrystalline cellulose, starch), combining agents (hydroxypropyl cellulose, polyvinyl pyrrolidone or magnesium metasilicate aluminate), disintegrating agents (e.g. cellulose calcium glycolate), lubricating agents (e.g. magnesium stearate), stabilizing agents, agents to assist dissolution (e.g. glutamic acid or aspartic acid), or the like. The agents may, if desired, be coated with coating agents (e.g. sugar, gelatin, hydroxypropyl cellulose or hydroxypropylmethyl cellulose phthalate), or be coated with two or more films. Further, coating may include containment within capsules of absorbable materials such as gelatin.

Liquid compositions for oral administration include pharmaceutically acceptable solutions, suspensions, emulsions, syrups and elixirs. In such compositions, the nitroxide antioxidant is dissolved, suspended or emulsified in a commonly used diluent (e.g. purified water, ethanol or mixture thereof). Furthermore, such liquid compositions may also comprise wetting agents or suspending agents, emulsifying agents, sweetening agents, flavoring agents, perfuming agents, preserving agents, buffer agents, or the like.

Injections for parenteral administration include solutions, suspensions, emulsions and solids which are dissolved or suspended. For injections, the nitroxide antioxidant can be dissolved, suspended and emulsified in a solvent. The solvents include, for example, distilled water for injection, physiological salt solution, vegetable oil, propylene glycol, polyethylene glycol, alcohol such as ethanol, or a mixture thereof. Moreover the injections can also include stabilizing agents, agents to assist dissolution (e.g. glutamic acid, aspartic acid or POLYSORBATE80™), suspending agents, emulsifying agents, soothing agents, buffer agents, preserving agents, etc. They can be sterilized in the final process or manufactured and prepared by sterile procedure. They can also be manufactured in the form of sterile solid compositions, such as a freeze-dried composition, and they may be sterilized or dissolved immediately before use in sterile distilled water for injection or some other solvent.

Other compositions for parenteral administration include liquids for external use, and ointment, endermic liniments, inhale, spray, suppositories for rectal administration and pessaries for vaginal administration which comprise the nixtroxide antioxidant and are administered by methods known in the art.

Spray compositions can comprise additional substances other than diluents: e.g. stabilizing agents (e.g. sodium sulfite hydride), isotonic buffers (e.g. sodium chloride, sodium citrate or citric acid). A small aerosol particle size useful for effective distribution of the medicament can be obtained by employing self-propelling compositions containing the drugs in micronized form dispersed in a propellant composition. Effective dispersion of the finely divided drug particles can be accomplished with the use of very small quantities of a suspending agent, present as a coating on the micronized drug particles. Evaporation of the propellant from the aerosol particles after spraying from the aerosol container leaves finely divided drug particles coated with a fine film of the suspending agent. In the micronized form, the average particle size can be less than about 5 microns. The propellant composition may employ, as the suspending agent, a fatty alcohol such as oleyl alcohol. The minimum quantity of suspending agent can be approximately 0.1 to 0.2 percent by weight of the total composition. The amount of suspending agent can be less than about 4 percent by weight of the total composition to maintain an upper particle size limit of less than 10 microns or 5 microns. Propellants that may be employed include hydrofluoroalkane propellants and chlorofluorocarbon propellants. Dry powder inhalation may also be employed.

EXAMPLES

The following examples are offered to illustrate but not to limit the invention.

In order to facilitate understanding, the specific embodiments are provided to help interpret the technical proposal, that is, these embodiments are only for illustrative purposes, but not in any way to limit the scope of the invention. Unless otherwise specified, embodiments do not indicate the specific conditions, are in accordance with the conventional conditions or the manufacturer's recommended conditions.

Example 1

Effects of Tempol on Expression of Genes Associated with the Apoptosis Pathway

To assess the effects of Tempol on gene expression, Tempol was administered to experimental mice at a dose of 5 mg/g of food from 14 months to 31 months after birth. Mice receiving the same food without the addition of Tempol were used as a negative control. At the age of 31 months, the experimental animals were sacrificed and the hearts were surgically removed. The expression of a broad spectrum of genes in the cardiac tissue was assessed using chip-based microarray technology. Such chips are well known in the art and are widely used to assess gene expression. The experimental results showed that five genes associated with the apoptosis pathway, Cd51, Perp, Unc5b, Bag5 and Bri3, exhibited statistically significant increase in expression. This result is shown in Table 1.

TABLE 1

Genes With Increased Expression In Cardiac Tissue After Tempol Administration

| Symbol | Gene title | Control mice | Tempol-treated mice | Fold change | P-value |
|---|---|---|---|---|---|
| Cd5l | CD5 antigen-like | 150 | 406 | 2.70 | 0.01 |
| Perp | TP53 apoptosis effector | 49 | 82 | 1.66 | 0.05 |
| Unc5b | Unc-5 homolog B | 103 | 172 | 1.66 | 0.01 |
| Bag5 | Bcl-2-associated athanogene 5 | 300 | 370 | 1.24 | 0.04 |
| Bri3 | Brain protein I3 | 1549 | 1835 | 1.18 | 0.00 |

Example 2

Treating Age-Related Decrease in Gene Expression

A 70-kilogram human subject over the age of 65 is identified for decreased expression level of Cd51, Perp, Unc5b, Bag5 or Bri3. The human subject is administered a dose of 1500 mg of Tempol (or a nitroxide antioxidant) per day for 180 days. This may be administered in a single dose, or may be administered as a number of smaller doses over a 24-hour mperiod: for example, three 500-mg doses at eight-hour intervals. Following treatment, the serum level of Cd51, Perp, Unc5b, Bag5 or Bri3, is increased.

Example 3

Treating Age-Related Decrease In Gene Expression

A human subject is administered a dose of 1500 mg of Tempol (or a nitroxide antioxidant) per day for 180 days. The human subject is a 70-kilogram human subject over the age of 65 with a decreased expression level of Cd51, Perp, Unc5b, Bag5 or Bri3. The human subject can be identified. The dose may be administered in a single dose, or may be administered as a number of smaller doses over a 24-hour period: for example, three 500-mg doses at eight-hour intervals. Following treatment, the serum level of Cd51, Perp, Unc5b, Bag5 or Bri3, is increased.

Example 4

Treating a Human Subject With Decreased Gene Expression

A 70-kilogram human subject is identified for decreased expression level of Cd51, Perp, Unc5b, Bag5 or Bri3. The human subject is administered a dose of 1500 mg of Tempol (or a nitroxide antioxidant) per day for 180 days. This may be administered in a single dose, or may be administered as a number of smaller doses over a 24-hour period: for example, three 500-mg doses at eight-hour intervals. Following treatment, the serum level of Cd51, Perp, Unc5b, Bag5 or Bri3, is increased.

Example 5

Treating a Human Subject with Decreased Gene Expression

A human subject is administered a dose of 1500 mg of Tempol (or a nitroxide antioxidant) per day for 180 days. The human subject is a 70-kilogram human subject with a decreased expression level of Cd51, Perp, Unc5b, Bag5 or Bri3. The human subject can be identified. The dose may be administered in a single dose, or may be administered as a number of smaller doses over a 24-hour period: for example, three 500-mg doses at eight-hour intervals. Following treatment, the serum level of Cd51, Perp, Unc5b, Bag5 or Bri3, is increased.

Example 6

Treating a Human Subject with a Disease (e.g., an Age-Related Disease)

A 70-kilogram human subject over the age of 65 and having a cardiovascular disease (or another age-related disease) is identified for decreased expression level of Cd51, Perp, Unc5b, Bag5 or Bri3. The human subject is administered a dose of 1500 mg of Tempol (or a nitroxide antioxidant) per day for 180 days. This may be administered in a single dose, or may be administered as a number of smaller doses over a 24-hour period: for example, three 500-mg doses at eight-hour intervals. Following treatment, the serum level of Cd51, Perp, Unc5b, Bag5 or Bri3, is increased.

Example 7

Treating a Human Subject with a Disease (e.g., an Age-Related Disease).

A human subject is administered a dose of 1500 mg of Tempol (or a nitroxide antioxidant) per day for 180 days. The human subject is a 70-kilogram human subject over the age of 65 and having a cardiovascular disease (or another age-related disease) with a decreased expression level of Cd51, Perp, Unc5b, Bag5 or Bri3. The human subject can be identified. The dose may be administered in a single dose, or may be administered as a number of smaller doses over a 24-hour period: for example, three 500-mg doses at eight-hour intervals. Following treatment, the serum level of Cd51, Perp, Unc5b, Bag5 or Bri3, is increased.

Example 8

Treating a Human Subject at Risk of Developing a Neurodegenerative Disease

A 70-kilogram human subject at risk of developing Parkinson's disease (or another neurodegenerative disease) is identified (e.g., the human subject may have decreased expression level of Cd51, Perp, Unc5b, Bag5 or Bri3. The human subject is administered a dose of 1500 mg of Tempol (or a nitroxide antioxidant) per day for 180 days. This may be administered in a single dose, or may be administered as a number of smaller doses over a 24-hour period: for example, three 500-mg doses at eight-hour intervals. Following treatment, the serum level of Cd51, Perp, Unc5b, Bag5 or Bri3, is increased.

Example 9

Treating a Human Subject at Risk of Developing a Neurodegenerative Disease

A human subject is administered a dose of 1500 mg of Tempol (or a nitroxide antioxidant) per day for 180 days. The human subject can be a 70-kilogram human subject at risk of developing Parkinson's disease (or another neurodegenerative disease). The human subject may have decreased expression level of Cd51, Perp, Unc5b, Bag5 or Bri3. The human subject can be identified. This may be administered in a single dose, or may be administered as a number of smaller doses over a 24-hour period: for example, three 500-mg doses at eight-hour intervals. Following treatment, the serum level of Cd51, Perp, Unc5b, Bag5 or Bri3, is increased.

Example 10

Treating a Human Subject with or at Risk of a Neurodegenerative Disease (e.g., Alzheimer's Disease)

A human subject is administered a dose of 1500 mg of Tempol (or a nitroxide antioxidant) per day for 180 days. The human subject may be a 70-kilogram human subject over the age of 65. The human subject may be at risk of developing a neurodegenerative disease (e.g., Alzheimer's Disease), may have symptoms of a neurodegenerative disease, and/or may have a neurodegenerative disease. The risk, the symptoms, or the neurodegenerative disease may be caused by decreased expression level of Bri3. The human subject can be identified. The dose may be administered in a single dose, or may be administered as a number of smaller doses over a 24-hour period: for example, three 500-mg doses at eight-hour intervals. Following treatment, the serum level of Bri3 is increased. Increased Bri3 expression can inhibit amyloid precursor protein (APP) processing and amyloid plaque deposition, thus suppressing or reversing development of the neurodegenerative disease.

Example 11

Treating a Human Subject at Risk of Developing Cancer

A 70-kilogram human subject at risk of developing colorectal cancer (or another cancer) is identified for decreased expression level of Cd51, Perp, Unc5b, Bag5 or Bri3. The human subject is administered a dose of 1500 mg of Tempol (or a nitroxide antioxidant) per day for 180 days. This may be administered in a single dose, or may be administered as a number of smaller doses over a 24-hour period: for example, three 500-mg doses at eight-hour intervals. Following treatment, the serum level of Cd51, Perp, Unc5b, Bag5 or Bri3, is increased.

Example 12

Treating a Human Subject at Risk of Developing Cancer

A human subject is administered a dose of 1500 mg of Tempol (or a nitroxide antioxidant) per day for 180 days. The human subject can be a 70-kilogram human subject at risk of developing colorectal cancer (or another cancer) with a decreased expression level of Cd51, Perp, Unc5b, Bag5 or Bri3. The human subject can be identified. This may be administered in a single dose, or may be administered as a number of smaller doses over a 24-hour period: for example, three 500-mg doses at eight-hour intervals. Following treatment, the serum level of Cd51, Perp, Unc5b, Bag5 or Bri3, is increased.

Example 13

Treating a Human Subject at Risk of Developing an Autoimmune Disease

A 70-kilogram human subject at risk of developing rheumatoid arthritis (or another autoimmune disease) is identified for decreased expression level of Cd51, Perp, UncSb, Bag5 or Bri3. The human subject is administered a dose of 1500 mg of Tempol (or a nitroxide antioxidant) per day for 180 days. This may be administered in a single dose, or may be administered as a number of smaller doses over a 24-hour period: for example, three 500-mg doses at eight-hour intervals. Following treatment, the serum level of Cd51, Perp, UncSb, Bag5 or Bri3, is increased.

Example 14

Treating a Human Subject at Risk of Developing an Autoimmune Disease

A human subject is administered a dose of 1500 mg of Tempol (or a nitroxide antioxidant) per day for 180 days. The human subject is a 70-kilogram human subject at risk of developing rheumatoid arthritis (or another autoimmune disease) with a decreased expression level of Cd51, Perp, Unc5b, Bag5 or Bri3. The human subject can be identified. This may be administered in a single dose, or may be administered as a number of smaller doses over a 24-hour period: for example, three 500-mg doses at eight-hour intervals. Following treatment, the serum level of Cd51, Perp, Unc5b, Bag5 or Bri3, is increased.

Example 15

Treating a Human Subject at Risk of Developing A Condition

A 70-kilogram human subject of 45 years old at risk of developing a condition due to aging is identified. The human subject is administered a dose of 1500 mg of Tempol (or a nitroxide antioxidant) per day for 180 days. This may be administered in a single dose, or may be administered as a number of smaller doses over a 24-hour period: for example, three 500-mg doses at eight-hour intervals. Following treatment, the serum level of Cd51, Perp, Unc5b, Bag5 or Bri3, is increased.

Example 16

Treating a Human Subject at Risk of Developing a Condition

A Human Subject is administered a dose of 1500 mg of Tempol (or a nitroxide antioxidant) per day for 180 days. The human subject can be a 70-kilogram human subject of 45 years old at risk of developing a condition due to aging. The human subject can be identified. This may be administered in a single dose, or may be administered as a number of smaller doses over a 24-hour period: for example, three 500-mg doses at eight-hour intervals. Following treatment, the serum level of Cd51, Perp, Unc5b, Bag5 or Bri3, is increased.

Example 17

Treating a Human Subject Having an Infection

A 70-kilogram human subject with an infection caused by *Mycobacterium tuberculosis* (or another bacteria, a fungus, a virus, or a parasite) is identified. The human subject is administered a dose of 1500 mg of Tempol (or a nitroxide antioxidant) per day for 180 days. This may be administered in a single dose, or may be administered as a number of smaller doses over a 24-hour period: for example, three 500-mg doses at eight-hour intervals. Following treatment, the serum level of Cd51, Perp, Unc5b, Bag5 or Bri3, is increased.

Example 18

Treating a Human Subject Having An Infection

A human subject is administered a dose of 1500 mg of Tempol (or a nitroxide antioxidant) per day for 180 days. The human subject can be a 70-kilogram human subject with an infection caused by *Mycobacterium tuberculosis* (or another bacteria, a fungus, a virus, or a parasite). The human subject can be identified. This may be administered in a single dose, or may be administered as a number of smaller doses over a 24-hour period: for example, three 500-mg doses at eight-hour intervals. Following treatment, the serum level of Cd51, Perp, Unc5b, Bag5 or Bri3, is increased.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., " a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., " a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of increasing expression level of Bri3, comprising:
   monitoring expression levels of Bri3 in an individual;
   confirming that said individual has a decreasing expression levels of Bri3; and
   administering to said individual an amount of a nitroxide antioxidant effective to increase the expression level of Bri3 relative to the decreasing expression levels.

2. The method of claim 1, wherein the nitroxide antioxidant is 4-hydroxy-2,2,6,6-tetramethylpiperidine-1-oxyl.

3. The method of claim 1, wherein the decreasing expression level of Bri3 is characterized by amyloid plaque formation.

4. The method of claim 1, wherein the increased expression level of Bri3 slows progression of said amyloid plaque formation.

* * * * *

UNITED STATES PATENT AND TRADEMARK OFFICE
CERTIFICATE OF CORRECTION

PATENT NO.        : 10,159,665 B2
APPLICATION NO.   : 15/815604
DATED             : December 25, 2018
INVENTOR(S)       : Louis Habash It is certified that error appears in the above-identified patent and that said Letters Patent is hereby corrected as shown below:

On the Title Page

Column 2, Item (57), Line 5, under Abstract, delete "BRI3" and insert --Bri3--.

Page 2, Column 1, Item (56), Line 38, under Other Publications, delete "CD4+" and insert --$CD4^+$--.

Page 2, Column 1, Item (56), Line 59, under Other Publications, delete "oft" and insert --of t--.

Page 2, Column 1, Item (56), Line 68, under Other Publications, delete "1255r1," and insert --125sr1,--.

Page 2, Column 2, Item (56), Line 24, under Other Publications, delete "BRI3" and insert --Bri3--.

Page 2, Column 2, Item (56), Line 40, under Other Publications, delete "PloS" and insert --PLoS--.

Page 3, Column 1, Item (56), Line 6, under Other Publications, delete "513238" and insert --13238--.

Page 3, Column 1, Item (56), Line 11, under Other Publications, delete "pink/-" and insert --pink1--.

Page 3, Column 1, Item (56), Line 63, under Other Publications, delete "Chnages" and insert --Changes--.

Page 3, Column 1, Item (56), Line 66, under Other Publications, delete "BRI3" and insert --Bri3--.

Page 4, Column 1, Item (56), Line 3, under Other Publications, delete "LoS" and insert -- PLoS--.

Page 4, Column 1, Item (56), Line 12, under Other Publications, delete "bri3," and insert --Bri3,--.

Signed and Sealed this
Twenty-eighth Day of April, 2020

Andrei Iancu
*Director of the United States Patent and Trademark Office*

CERTIFICATE OF CORRECTION (continued)
U.S. Pat. No. 10,159,665 B2

In the Specification

Column 8, Line 1, delete "ataxis," and insert --ataxia,--.

Column 8, Line 24, delete "tetramethlpiperidine" and insert --tetramethylpiperidine--.

Column 8, Line 64, delete "tetramethlpiperidine" and insert --tetramethylpiperidine--.

Column 9, Line 23, delete "tetramethlpiperidine" and insert --tetramethylpiperidine--.

Column 11, Line 21, delete "(lllumina," and insert --(Illumina,--.

Column 12, Line 5, delete "MRCS," and insert --BIRC5,--.

Column 12, Line 59, delete "LoS" and insert --PLoS--.

Column 17, Line 5, delete "BRI$_3$" and insert --Bri3--.

Column 20, Line 60, delete "MM" and insert --MRI--.

Column 20, Line 60, delete "MM;" and insert --MRI;--.

Column 22, Line 43, delete "lymphangioendothelio-sarcoma," and insert --lymphangioendothelioma-sarcoma,--.

Column 24, Line 6, delete "Burkitts" and insert --Burkitt's--.

Column 26, Line 3, delete "choleosatatis," and insert --cholestasis,--.

Column 26, Lines 25-26, delete "abetalipoprotemia," and insert --abetalipoproteinemia,--.

Column 27, Lines 29-30, delete "Hallerrorden-Spatz disease," and insert --Hallervorden-Spatz disease,--.

Column 27, Line 31, delete "hemachromatosis," and insert --hemochromatosis,--.

Column 27, Line 52, delete "lipidema," and insert --lipedema,--.

Column 27, Lines 52-53, delete "lymphederma," and insert --lymphedema,--.

Column 27, Line 64, delete "myelodyplastic" and insert --myelodysplastic--.

Column 28, Line 4, delete "epidydimitis," and insert --epididymitis,--.

Column 28, Line 25, delete "Raynoud's" and insert --Raynaud's--.

CERTIFICATE OF CORRECTION (continued)
U.S. Pat. No. 10,159,665 B2

Column 28, Line 34, delete "Sjorgren's" and insert --Sjogren's--.

Column 28, Line 61, delete "hemaphagocytic" and insert --hemophagocytic--.

Column 30, Line 44, delete "ataxis," and insert --ataxia,--.

Column 31, Line 21, delete "CH3" and insert --$CH_3$--.

Column 31, Line 21, delete "R2" and insert --$R_2$--.

Column 31, Line 22, delete "C2H5" and insert --$C_2H_5$--.

Column 34, Line 52, delete "mperiod:" and insert --period:--.

Column 36, Line 8 (Approx.), delete "(e.g.," and insert --e.g.,--.

Column 37, Line 33, delete "UncSb," and insert --Unc5b,--.

Column 37, Line 40, delete "UncSb," and insert --Unc5b,--.